United States Patent
Kendrick et al.

(10) Patent No.: US 11,957,614 B2
(45) Date of Patent: Apr. 16, 2024

(54) URINE COLLECTION BAGS FOR USE WITH CATHETER PRODUCTS, KITS INCORPORATING THE SAME, AND METHODS THEREFOR

(71) Applicant: CONVATEC TECHNOLOGIES INC., Las Vegas, NV (US)

(72) Inventors: Drew A. Kendrick, Deeside (GB); Julie Lambrethsen, Deeside (GB)

(73) Assignee: ConvaTec Technologies, Inc., Las Vegas, NV (US)

( * ) Notice: Subject to any disclaimer, the term of this patent is extended or adjusted under 35 U.S.C. 154(b) by 0 days.

(21) Appl. No.: 16/897,498

(22) Filed: Jun. 10, 2020

(65) Prior Publication Data
US 2021/0022908 A1    Jan. 28, 2021

Related U.S. Application Data

(60) Provisional application No. 62/860,173, filed on Jun. 11, 2019.

(51) Int. Cl.
*A61F 5/44* (2006.01)
*A61M 25/00* (2006.01)

(52) U.S. Cl.
CPC .............. *A61F 5/44* (2013.01); *A61F 5/4405* (2013.01); *A61M 25/0017* (2013.01); *A61M 2210/1089* (2013.01)

(58) Field of Classification Search
CPC .. A61F 5/44; A61F 5/4405; A61F 2005/4402; A61M 25/0017; A61M 2210/1089
See application file for complete search history.

(56) References Cited

U.S. PATENT DOCUMENTS

| 4,246,909 A * | 1/1981 | Wu ................. A61M 1/70 600/580 |
| 4,723,944 A | 2/1988 | Jensen |
| 5,333,736 A | 8/1994 | Kawamura |
| 6,849,070 B1 | 2/2005 | Hansen et al. |
| 8,475,434 B2 | 7/2013 | Fröjd |
| 10,207,076 B2 | 2/2019 | Foley et al. |

(Continued)

FOREIGN PATENT DOCUMENTS

| DE | 202013006481 U1 | 8/2013 |
| EP | 3001976 A1 | 4/2016 |

(Continued)

OTHER PUBLICATIONS

US 11,433,217 B2, 09/2022, Klein (withdrawn)

(Continued)

*Primary Examiner* — Kai H Weng
*Assistant Examiner* — Nhu Q. Tran
(74) *Attorney, Agent, or Firm* — Taft Stettinius & Hollister LLP; Ryan O. White; Derek B. Lavender

(57) ABSTRACT

Urine collection bags, kits including urine collection bags, methods of collecting urine, and methods of manufacturing urine collection bags are disclosed herein. A urine collection bag includes an outer profile, an inner profile, and first and second external layers. The first and second external layers are sealed around a first periphery to define the inner profile. The inner profile has a container portion and an elongated portion.

25 Claims, 7 Drawing Sheets

(56) References Cited

U.S. PATENT DOCUMENTS

| | | |
|---|---|---|
| 10,426,584 B2 | 10/2019 | McClurg |
| 10,426,654 B2 | 10/2019 | Ugarte |
| 10,426,918 B2 | 10/2019 | Foley et al. |
| 10,426,919 B2 | 10/2019 | Erbey, II et al. |
| 10,434,282 B2 | 10/2019 | Kearns et al. |
| 10,441,454 B2 | 10/2019 | Tanghoej et al. |
| 10,449,083 B2 | 10/2019 | Pierson |
| 10,449,327 B2 | 10/2019 | Overtoom |
| 10,449,328 B2 | 10/2019 | Tanghoej et al. |
| 10,449,329 B2 | 10/2019 | Foley et al. |
| 10,463,466 B2 | 11/2019 | Cullison |
| 10,463,833 B2 | 11/2019 | Clarke et al. |
| 10,470,861 B2 | 11/2019 | Khamis et al. |
| 10,485,483 B1 | 11/2019 | Brody |
| 10,485,644 B2 | 11/2019 | Orr et al. |
| 10,493,230 B2 | 12/2019 | Guldager et al. |
| 10,493,231 B2 | 12/2019 | McMenamin et al. |
| 10,493,252 B2 | 12/2019 | Browne et al. |
| 10,506,965 B2 | 12/2019 | Cooper et al. |
| 10,512,713 B2 | 12/2019 | Erbey, II et al. |
| 10,531,894 B2 | 1/2020 | Connors et al. |
| 10,531,976 B2 | 1/2020 | Palmer |
| 10,548,523 B2 | 2/2020 | Ahmadi et al. |
| 10,569,046 B2 | 2/2020 | Steindahl et al. |
| 10,569,047 B2 | 2/2020 | Farrell et al. |
| 10,569,051 B2 | 2/2020 | Conway et al. |
| 10,575,935 B2 | 3/2020 | Wei et al. |
| 10,588,774 B2 | 3/2020 | Alhaqqan |
| 10,589,061 B2 | 3/2020 | Palmer |
| 10,589,093 B2 | 3/2020 | Imran |
| 10,610,344 B2 | 4/2020 | Shapiro et al. |
| 10,610,664 B2 | 4/2020 | Erbey, II et al. |
| 10,617,843 B2 | 4/2020 | Paz |
| 10,631,788 B2 | 4/2020 | Brody |
| 10,639,451 B2 | 5/2020 | Kearns et al. |
| 10,639,452 B2 | 5/2020 | Linares et al. |
| 10,646,688 B2 | 5/2020 | Hannon et al. |
| 10,667,894 B2 | 6/2020 | Forsell |
| 10,668,249 B2 | 6/2020 | Douglas et al. |
| 10,675,134 B2 | 6/2020 | Herrera et al. |
| 10,675,435 B2 | 6/2020 | Herrera et al. |
| 10,682,214 B2 | 6/2020 | Sufyan et al. |
| 10,690,655 B2 | 6/2020 | Duval |
| 10,702,671 B2 | 7/2020 | Terry |
| 10,709,819 B2 | 7/2020 | Littleton et al. |
| D893,706 S | 8/2020 | Lessmann |
| 10,736,491 B2 | 8/2020 | Truckai |
| 10,737,057 B1 | 8/2020 | Mikhail et al. |
| 10,744,298 B1 | 8/2020 | Bello et al. |
| 10,751,493 B2 | 8/2020 | Gregory et al. |
| 10,758,704 B2 | 9/2020 | Hickmott et al. |
| 10,765,833 B2 | 9/2020 | Kearns |
| 10,765,834 B2 | 9/2020 | Erbey, II et al. |
| 10,772,755 B2 | 9/2020 | Gregory |
| 10,780,243 B2 | 9/2020 | Reyes |
| 10,780,244 B2 | 9/2020 | Conway et al. |
| 10,780,245 B2 | 9/2020 | Schonfeldt |
| 10,799,687 B1 | 10/2020 | Scott |
| 10,807,287 B2 | 10/2020 | Rolsted et al. |
| 10,814,097 B2 | 10/2020 | Palmer |
| 11,376,395 B2 | 7/2022 | Montes de Oca et al. |
| 11,420,015 B2 | 8/2022 | Palmer |
| 11,420,016 B2 | 8/2022 | Palmer |
| 11,420,017 B2 | 8/2022 | Hilton et al. |
| 11,446,468 B2 | 9/2022 | Havard et al. |
| 11,458,283 B2 | 10/2022 | Fletter et al. |
| 11,484,688 B2 | 11/2022 | Sremcevic |
| 11,490,983 B2 | 11/2022 | Knapp et al. |
| 11,534,573 B2 | 12/2022 | Hannon et al. |
| 11,534,577 B2 | 12/2022 | House |
| 11,541,205 B2 | 1/2023 | Erbey, II et al. |
| 11,547,833 B2 | 1/2023 | Murray et al. |
| 11,554,038 B2 | 1/2023 | O'Flynn et al. |
| 11,583,600 B2 | 2/2023 | Paul et al. |
| 11,602,453 B2 | 3/2023 | Palmer |
| 11,617,807 B2 | 4/2023 | Paul et al. |
| 11,617,808 B2 | 4/2023 | Paul et al. |
| 11,623,020 B2 | 4/2023 | O'Mahony |
| 11,678,968 B2 | 6/2023 | Behan |
| 2003/0018293 A1 | 1/2003 | Tanghoj et al. |
| 2003/0083644 A1 | 5/2003 | Avaltroni |
| 2004/0078940 A1* | 4/2004 | Ishizaki ............... B65D 33/255 24/400 |
| 2004/0236293 A1* | 11/2004 | Tanghoj .................. A61F 5/44 604/327 |
| 2005/0043715 A1 | 2/2005 | Nestenborg et al. |
| 2006/0111681 A1 | 5/2006 | Vernon |
| 2006/0163097 A1 | 7/2006 | Murray et al. |
| 2009/0137985 A1 | 5/2009 | Tanghoej et al. |
| 2009/0163884 A1* | 6/2009 | Kull-Osterlin ...... A61M 25/002 53/461 |
| 2010/0312203 A1 | 12/2010 | House |
| 2010/0324535 A1 | 12/2010 | Triel |
| 2011/0190736 A1 | 8/2011 | Young et al. |
| 2011/0224653 A1 | 9/2011 | Torstensen |
| 2012/0046623 A1 | 2/2012 | Bordeau |
| 2012/0116335 A1 | 5/2012 | Tanghoej |
| 2013/0138135 A1 | 5/2013 | Rosen et al. |
| 2013/0161208 A1 | 6/2013 | Gustavsson |
| 2013/0161227 A1 | 6/2013 | Gustavsson |
| 2013/0261608 A1 | 10/2013 | Tanghoj |
| 2014/0066905 A1 | 3/2014 | Young |
| 2014/0288517 A1 | 9/2014 | Tsai et al. |
| 2014/0336569 A1 | 11/2014 | Gobel |
| 2014/0378951 A1 | 12/2014 | Dye |
| 2015/0133898 A1 | 5/2015 | Murray et al. |
| 2015/0273180 A1 | 10/2015 | Schonfeldt |
| 2015/0273747 A1 | 10/2015 | Montes de Oca Balderas et al. |
| 2015/0290421 A1 | 10/2015 | Glickman et al. |
| 2015/0297862 A1 | 10/2015 | Sadik et al. |
| 2015/0320970 A1 | 11/2015 | Foley et al. |
| 2016/0067445 A1 | 3/2016 | Murray et al. |
| 2016/0176622 A1* | 6/2016 | Vertsteylen .......... A61G 17/047 206/205 |
| 2016/0184551 A1 | 6/2016 | Nyman et al. |
| 2016/0206469 A1 | 7/2016 | Prezelin |
| 2016/0287759 A1 | 10/2016 | Clarke et al. |
| 2016/0317715 A1 | 11/2016 | Rostami et al. |
| 2016/0325903 A1 | 11/2016 | Doerschner et al. |
| 2017/0000978 A1 | 1/2017 | Murray et al. |
| 2017/0021128 A1 | 1/2017 | Erbey, II et al. |
| 2017/0105826 A1 | 4/2017 | Erikstrup |
| 2017/0319373 A1* | 11/2017 | Mitts ..................... A61F 5/4407 |
| 2017/0348137 A1 | 12/2017 | Hvid et al. |
| 2017/0348138 A1 | 12/2017 | Hvid et al. |
| 2018/0015250 A1 | 1/2018 | Tsukada et al. |
| 2018/0021481 A1 | 1/2018 | Yin et al. |
| 2018/0050173 A1 | 2/2018 | Kearns |
| 2018/0071482 A1 | 3/2018 | Fitzpatrick et al. |
| 2018/0193618 A1 | 7/2018 | Erbey et al. |
| 2018/0326179 A1 | 11/2018 | Erbey et al. |
| 2018/0333289 A1 | 11/2018 | Paley |
| 2018/0369474 A1 | 12/2018 | Falleboe et al. |
| 2019/0099583 A1 | 4/2019 | Charlez et al. |
| 2019/0126004 A1 | 5/2019 | OBrien et al. |
| 2019/0142394 A1* | 5/2019 | Klaassen ............ A61B 10/0096 600/573 |
| 2019/0151610 A1 | 5/2019 | Fletter |
| 2019/0224402 A1 | 7/2019 | Henry et al. |
| 2019/0240060 A1 | 8/2019 | He et al. |
| 2019/0247549 A1 | 8/2019 | Nielsen |
| 2019/0314044 A1 | 10/2019 | Long et al. |
| 2019/0314188 A1 | 10/2019 | Barrientos |
| 2019/0314190 A1 | 10/2019 | Sanchez et al. |
| 2019/0321587 A1 | 10/2019 | McMenamin et al. |
| 2019/0321589 A1 | 10/2019 | Bonneau |
| 2019/0358075 A1 | 11/2019 | Scharich, III et al. |
| 2019/0358435 A1 | 11/2019 | Andersin et al. |
| 2019/0365561 A1 | 12/2019 | Newton et al. |
| 2019/0366038 A1 | 12/2019 | Denman et al. |
| 2019/0374324 A1 | 12/2019 | Luleci |
| 2019/0381291 A1 | 12/2019 | Feld |
| 2019/0388659 A1 | 12/2019 | Ruel |
| 2020/0001045 A1 | 1/2020 | McIntyre |

(56) References Cited

U.S. PATENT DOCUMENTS

| | | |
|---|---|---|
| 2020/0001049 A1 | 1/2020 | House |
| 2020/0016380 A1 | 1/2020 | Murray et al. |
| 2020/0022636 A1 | 1/2020 | Suehara et al. |
| 2020/0030135 A1 | 1/2020 | Woodyard |
| 2020/0030582 A1 | 1/2020 | Dong |
| 2020/0030595 A1 | 1/2020 | Boukidjian et al. |
| 2020/0037832 A1 | 2/2020 | Wang et al. |
| 2020/0054800 A1 | 2/2020 | Wilbourn et al. |
| 2020/0094017 A1 | 3/2020 | Erbey, II et al. |
| 2020/0101280 A1 | 4/2020 | Peddicord |
| 2020/0113779 A1 | 4/2020 | Nagamura et al. |
| 2020/0129731 A1 | 4/2020 | Brar et al. |
| 2020/0139109 A1 | 5/2020 | Imran |
| 2020/0146799 A1 | 5/2020 | Connors et al. |
| 2020/0146871 A1 | 5/2020 | Palmer |
| 2020/0155261 A1 | 5/2020 | OFlynn et al. |
| 2020/0163543 A1 | 5/2020 | Schutt et al. |
| 2020/0163699 A1 | 5/2020 | Bacich et al. |
| 2020/0179644 A1 | 6/2020 | Guldbaek |
| 2020/0179665 A1 | 6/2020 | Orr et al. |
| 2020/0188631 A1 | 6/2020 | Hannon et al. |
| 2020/0206389 A1 | 7/2020 | Vange |
| 2020/0206411 A1 | 7/2020 | Henry et al. |
| 2020/0206468 A1 | 7/2020 | Olson et al. |
| 2020/0206470 A1 | 7/2020 | Orr et al. |
| 2020/0214820 A1 | 7/2020 | Bunch et al. |
| 2020/0215303 A1 | 7/2020 | Erbey, II et al. |
| 2020/0222188 A1 | 7/2020 | Smith et al. |
| 2020/0222220 A1 | 7/2020 | Kappus et al. |
| 2020/0222659 A1 | 7/2020 | Schertiger et al. |
| 2020/0222660 A1 | 7/2020 | Erbey, II et al. |
| 2020/0222674 A1 | 7/2020 | Inoue et al. |
| 2020/0229964 A1 | 7/2020 | Staali et al. |
| 2020/0230349 A1 | 7/2020 | McMenamin et al. |
| 2020/0230356 A1 | 7/2020 | Utas et al. |
| 2020/0230382 A1 | 7/2020 | Siebert |
| 2020/0238048 A1 | 7/2020 | Palmer |
| 2020/0246587 A1 | 8/2020 | Tal et al. |
| 2020/0246589 A1 | 8/2020 | Starr |
| 2020/0246594 A1 | 8/2020 | Miller |
| 2020/0254215 A1 | 8/2020 | Portela et al. |
| 2020/0261692 A1 | 8/2020 | Palmer |
| 2020/0262868 A1 | 8/2020 | Ricca et al. |
| 2020/0268947 A1 | 8/2020 | Erbey, II et al. |
| 2020/0276046 A1 | 9/2020 | Staali et al. |
| 2020/0276410 A1 | 9/2020 | Son |
| 2020/0281760 A1 | 9/2020 | Fleming |
| 2020/0282092 A1 | 9/2020 | Paul et al. |
| 2020/0306502 A1 | 10/2020 | Luning et al. |
| 2020/0315445 A1 | 10/2020 | Cheng et al. |
| 2020/0324006 A1 | 10/2020 | Paul et al. |
| 2020/0330724 A1 | 10/2020 | Mikhail et al. |
| 2020/0375781 A1 | 12/2020 | Staali et al. |
| 2021/0170149 A1 | 6/2021 | Erbey et al. |
| 2021/0177565 A1 | 6/2021 | Conway et al. |
| 2021/0178026 A1 | 6/2021 | Farrell et al. |
| 2021/0187238 A1 | 6/2021 | OBrien et al. |
| 2021/0196923 A1 | 7/2021 | Palmer |
| 2021/0204968 A1 | 7/2021 | Yurek |
| 2021/0228823 A1 | 7/2021 | Mohiuddin et al. |
| 2021/0228836 A1 | 7/2021 | Terry |
| 2021/0228837 A1 | 7/2021 | Palmer |
| 2021/0244910 A1 | 8/2021 | OBrien et al. |
| 2021/0244912 A1 | 8/2021 | Paz et al. |
| 2021/0251798 A1 | 8/2021 | Mitts |
| 2021/0260332 A1 | 8/2021 | Panesar et al. |
| 2021/0275727 A1 | 9/2021 | Farrell et al. |
| 2021/0275775 A1 | 9/2021 | Hong et al. |
| 2021/0283367 A1 | 9/2021 | Peters |
| 2021/0290893 A1 | 9/2021 | Palmer |
| 2021/0290894 A1 | 9/2021 | Palmer |
| 2021/0290910 A1 | 9/2021 | Orr et al. |
| 2021/0322720 A1 | 10/2021 | Hunt |
| 2021/0330929 A1 | 10/2021 | Kendrick et al. |
| 2021/0330938 A1 | 10/2021 | Kendrick et al. |
| 2021/0338979 A1 | 11/2021 | Palmer |
| 2021/0346644 A1 | 11/2021 | Kendrick et al. |
| 2021/0346645 A1 | 11/2021 | McMenamin et al. |
| 2021/0346647 A1 | 11/2021 | Kendrick et al. |
| 2021/0346648 A1 | 11/2021 | Kendrick et al. |
| 2021/0353449 A1 | 11/2021 | Sharma et al. |
| 2021/0361908 A1 | 11/2021 | Erbey et al. |
| 2021/0370018 A1 | 12/2021 | Murray et al. |
| 2021/0370019 A1 | 12/2021 | Erbey et al. |
| 2021/0378811 A1 | 12/2021 | Forsell |
| 2021/0386965 A1 | 12/2021 | McMenamin et al. |
| 2021/0386969 A1 | 12/2021 | OFlynn |
| 2021/0402135 A1 | 12/2021 | McMenamin et al. |
| 2022/0001136 A1 | 1/2022 | Hede et al. |
| 2022/0008626 A1 | 1/2022 | Farrell et al. |
| 2022/0023585 A1 | 1/2022 | Schertiger et al. |
| 2022/0040449 A1 | 2/2022 | Sremcevic |
| 2022/0047844 A1 | 2/2022 | Gobel |
| 2022/0054295 A1 | 2/2022 | Becker |
| 2022/0054798 A1 | 2/2022 | Erbey et al. |
| 2022/0087698 A1 | 3/2022 | Yurek |
| 2022/0118161 A1 | 4/2022 | Bager et al. |
| 2022/0133426 A1 | 5/2022 | OFlynn et al. |
| 2022/0184342 A1 | 6/2022 | Erbey et al. |
| 2022/0211891 A1 | 7/2022 | Paul et al. |
| 2022/0211973 A1 | 7/2022 | Palmer |
| 2022/0226602 A1 | 7/2022 | Farrell |
| 2022/0233808 A1 | 7/2022 | Farrell et al. |
| 2022/0241553 A1 | 8/2022 | Farrell et al. |
| 2022/0241557 A1 | 8/2022 | Erbey et al. |
| 2022/0288350 A1 | 9/2022 | Montes de Oca et al. |
| 2022/0362515 A1 | 11/2022 | Erbey et al. |
| 2022/0379075 A1 | 12/2022 | Hilton et al. |
| 2022/0387751 A1 | 12/2022 | Havard et al. |
| 2023/0095287 A1 | 3/2023 | O'Brien et al. |
| 2023/0099846 A1 | 3/2023 | Hannon et al. |
| 2023/0133471 A1 | 5/2023 | House |
| 2023/0157800 A1 | 5/2023 | Newman et al. |

FOREIGN PATENT DOCUMENTS

| | | |
|---|---|---|
| EP | 3100758 A1 | 12/2016 |
| EP | 3315159 A1 | 5/2018 |
| EP | 3351208 A1 | 7/2018 |
| EP | 3613457 A1 | 2/2020 |
| EP | 3283136 B1 | 6/2021 |
| EP | 3854427 A1 | 7/2021 |
| EP | 3854438 A1 | 7/2021 |
| EP | 3862031 A1 | 8/2021 |
| EP | 3519031 B1 | 9/2021 |
| EP | 2750749 B1 | 10/2021 |
| EP | 3668555 B1 | 10/2021 |
| EP | 3727550 B1 | 10/2021 |
| EP | 3886960 A1 | 10/2021 |
| EP | 3892320 A1 | 10/2021 |
| EP | 3897480 A1 | 10/2021 |
| EP | 3912669 A1 | 11/2021 |
| EP | 3914329 A1 | 12/2021 |
| EP | 3921009 A1 | 12/2021 |
| EP | 3943140 A1 | 1/2022 |
| EP | 3952969 A1 | 2/2022 |
| EP | 3952973 A1 | 2/2022 |
| EP | 3955863 A1 | 2/2022 |
| EP | 3576689 B1 | 3/2022 |
| EP | 3958918 A1 | 3/2022 |
| EP | 3725355 B1 | 5/2022 |
| EP | 3727549 B1 | 6/2022 |
| EP | 4005479 A1 | 6/2022 |
| EP | 4015008 A1 | 6/2022 |
| EP | 2515988 B2 | 7/2022 |
| EP | 2968842 B1 | 7/2022 |
| EP | 3593850 B1 | 9/2022 |
| EP | 3257546 B1 | 10/2022 |
| EP | 4085962 A1 | 11/2022 |
| EP | 4088749 A1 | 11/2022 |
| EP | 2688629 B1 | 12/2022 |
| EP | 3793626 B1 | 12/2022 |
| EP | 4176908 A1 | 5/2023 |
| EP | 3194000 B1 | 6/2023 |

(56) References Cited

FOREIGN PATENT DOCUMENTS

| | | | | |
|---|---|---|---|---|
| EP | 3352831 | B1 | 6/2023 | |
| EP | 3572113 | B1 | 6/2023 | |
| EP | 3914329 | B1 | 6/2023 | |
| GB | 2336830 | A * | 11/1999 | ............... A61F 5/44 |
| GB | 2540125 | B | 1/2017 | |
| GB | 2579273 | B | 2/2023 | |
| JP | H5-49643 | U | 6/1993 | |
| JP | 2020011103 | A | 1/2020 | |
| WO | 2009048375 | A1 | 4/2009 | |
| WO | 2011051439 | A1 | 5/2011 | |
| WO | 2018134591 | A1 | 7/2018 | |
| WO | 2018143487 | A1 | 8/2018 | |
| WO | 2019004304 | A1 | 1/2019 | |
| WO | 2019014344 | A1 | 1/2019 | |
| WO | 2019038732 | A1 | 2/2019 | |
| WO | 2019038734 | A1 | 2/2019 | |
| WO | 2019106581 | A2 | 6/2019 | |
| WO | 2019123004 | A1 | 6/2019 | |
| WO | 2019184222 | A1 | 10/2019 | |
| WO | 2019222644 | A1 | 11/2019 | |
| WO | 2019229597 | A1 | 12/2019 | |
| WO | 2020015804 | A1 | 1/2020 | |
| WO | 2020093698 | A1 | 5/2020 | |
| WO | 2020110046 | A1 | 6/2020 | |
| WO | 2020110051 | A1 | 6/2020 | |
| WO | 2020132731 | A1 | 7/2020 | |
| WO | 2020136503 | A1 | 7/2020 | |
| WO | 2020136645 | A1 | 7/2020 | |
| WO | 2020144302 | A1 | 7/2020 | |
| WO | 2020160738 | A1 | 8/2020 | |
| WO | 2020078711 | A1 | 9/2020 | |
| WO | 2020173531 | A1 | 9/2020 | |
| WO | 2020173942 | A1 | 9/2020 | |
| WO | 2020214944 | A1 | 10/2020 | |
| WO | 2021108115 | A1 | 6/2021 | |
| WO | 2021127040 | A1 | 6/2021 | |
| WO | 2021154444 | A1 | 8/2021 | |
| WO | 2021160751 | A1 | 8/2021 | |
| WO | 2021183718 | A1 | 9/2021 | |
| WO | 2021221919 | A1 | 11/2021 | |
| WO | 2021231724 | A1 | 11/2021 | |
| WO | 2021240266 | A1 | 12/2021 | |
| WO | 2021242487 | A1 | 12/2021 | |

OTHER PUBLICATIONS

US 11,433,219 B2, 09/2022, Erbey et al. (withdrawn)
David Hame, Pyramid Drainage Bag, Apr. 29, 1998 (Year: 1998).*
International Application No. PCT/US2018/067363.
International Application No. PCT/US2018/067366.
Invitation to Pay Additional Fees; International Searching Authority; International Patent Application No. PCT/US2020/036933; dated Aug. 21, 2020; 2 pages.
International Preliminary Report on Patentability; International Searching Authority; International Patent Application No. PCT/US2020/036933; dated Jun. 1, 2021; 20 pages.
Colombian Office Action, Superintendencia de Industria y Comercio, Colombian Patent Application No. NC2021/0016076, dated Jan. 16, 2023, 9 pages.
Chinese Office Action, China National Intellectual Property Administration, Chinese Patent Application No. 202080043560.9, Aug. 30, 2023, 10 pages.
Colombian Office Action, Superintendencia de Industria y Comercio, Colombian Patent Application No. NC2021/0016076, Feb. 23, 2024, 20 pages.
Japanese Office Action, Japan Patent Office, Japanese Patent Application No. 2021-573349, Feb. 27, 2024, 11 pages.
Singaporean Search Report, Intellectual Property Office of Singapore, Singaporean Patent Application No. 11202111856R, Feb. 28, 2024, 2 pages.
Singaporean Written Opinion, Intellectual Property Office of Singapore, Singaporean Patent Application No. 11202111856R, Feb. 28, 2024, 6 pages.

* cited by examiner

URINE COLLECTION BAGS FOR USE WITH CATHETER PRODUCTS, KITS INCORPORATING THE SAME, AND METHODS THEREFOR

CROSS-REFERENCE TO RELATED APPLICATION

This application claims priority to, and the benefit of, U.S. Provisional Patent Application Ser. No. 62/860,173 entitled "Urine Collection Bag for use with Catheter Products," which was filed on Jun. 11, 2019. That provisional application is incorporated herein by reference in its entirety.

FIELD OF THE DISCLOSURE

The present disclosure relates, generally, to urinary catheter systems, and, more specifically, to urine collection bags included in urinary catheter systems.

BACKGROUND

Urinary catheter systems may be used by patients who are hospitalized, bed-ridden, or suffer from urinary incontinence. Such systems generally include a urinary catheter and a urine collection bag.

SUMMARY

The present disclosure may comprise one or more of the following features and combinations thereof.

According to one aspect of the present disclosure, a urine collection bag may include an outer profile, an inner profile, and first and second external layers that are sealed around a first periphery to define the inner profile. The inner profile may include a container portion for holding urine and an elongated portion capable of receiving a catheter through an opening in the elongated portion.

In some embodiments, the elongated portion may be capable of receiving a male catheter or other urinary catheter(s) designed for insertion into, and collection from, a male urethra. Additionally, in some embodiments, the elongated portion may be capable of receiving a female catheter or other urinary catheter(s) designed for insertion into, and collection from, a female urethra.

In some embodiments, the first external layer and the second external layer may be welded at the first periphery to define the inner profile.

In some embodiments, the first external layer and the second external layer may be sealed around a second periphery to define the outer profile.

In some embodiments, the first external layer and the second external layer may be welded at a second periphery to define the outer profile.

In some embodiments, the urine collection bag may include a first webbing section positioned between the inner profile and the outer profile.

In some embodiments, the first webbing section may include a region of the first external layer and the second external layer welded together.

In some embodiments, the first webbing section may include a first aperture.

In some embodiments, the urine collection bag may include a first aperture.

In some embodiments, the first aperture may be positioned between the inner profile and the outer profile.

In some embodiments, the elongated portion and the first aperture may be arranged such that at least a portion of the elongated portion is threadable through the first aperture.

In some embodiments, the urine collection bag may include a second webbing section positioned between the inner profile and the outer profile.

In some embodiments, the second webbing section may include a region of the first external layer and the second external layer welded together.

In some embodiments, the second webbing section may include a second aperture.

In some embodiments, the urine collection bag may include a second aperture.

In some embodiments, the second aperture may be positioned between the inner profile and the outer profile.

In some embodiments, the urine collection bag may include a third webbing section positioned between the inner profile and the outer profile.

In some embodiments, the third webbing section may include a region of the first external layer and the second external layer welded together.

In some embodiments, the third webbing section may include a perforation.

In some embodiments, the urine collection bag may include a perforation.

In some embodiments, the perforation may be positioned between the inner profile and the outer profile.

In some embodiments, the urine collection bag may include a valve.

In some embodiments, the valve may be a one-way valve.

In some embodiments, the valve may include polyvinyl chloride.

In some embodiments, the valve may include a first internal layer and a second internal layer positioned within the elongated portion.

In some embodiments, the first internal layer and the second internal layer may be welded between the first external layer and the second external layer.

In some embodiments, in use, the catheter may be positioned between the first internal layer and the second internal layer.

In some embodiments, the first internal layer may include one or more welds.

In some embodiments, the first internal layer, the second internal layer, the first external layer, and the second external layer may be sealed together on two or more sides of each layer.

In some embodiments, the seal may include a weld.

In some embodiments, the first internal layer may include polyvinyl chloride.

In some embodiments, the second internal layer may include polyvinyl chloride.

In some embodiments, the urine collection bag may include a notch at the opening to facilitate insertion of the catheter into the elongated portion.

In some embodiments, the first external layer may be shorter than the second external layer at the opening to create the notch.

In some embodiments, the elongated portion may include a tapered profile.

In some embodiments, the tapered profile may be formed by welding the first external layer with the second external layer.

In some embodiments, the urine collection bag may include a fourth webbing section positioned between the inner profile and the outer profile in the elongated portion.

In some embodiments, the fourth webbing section may include a region of the first external layer and the second external layer welded together.

In some embodiments, the first external layer may have a thickness of about 75 microns to about 225 microns.

In some embodiments, the second external layer may have a thickness of about 75 microns to about 225 microns.

In some embodiments, the first external layer may include polyvinyl chloride, polypropylene, polyethylene, ethylene-vinyl acetate, or a combination thereof.

In some embodiments, the first external layer may include polyvinyl chloride.

In some embodiments, the second external layer may include polyvinyl chloride, polypropylene, polyethylene, ethylene-vinyl acetate, or a combination thereof.

In some embodiments, the second external layer may include polyvinyl chloride.

In some embodiments, a bottom of the container portion may be folded.

In some embodiments, the urine collection bag may be capable of standing upright when filled with at least about 20% fill capacity.

In some embodiments, the container portion may be capable of holding at least about 500 mL of urine.

In some embodiments, the container portion may include at least four sides, and not one of the at least four sides may be parallel to another one of the at least four sides.

In some embodiments, at least two of the at least four sides may be at least substantially straight.

In some embodiments, each of the at least four sides may have a length of at least about 1 cm and a curvature of less than about two degrees.

In some embodiments, each of the at least four sides may have a length of at least about 5 cm and a curvature of less than about two degrees.

According to another aspect of the present disclosure, a kit may include any urine collection bag disclosed herein and a catheter.

In some embodiments, the catheter may include a distal end, a proximal end, and a length therebetween, and the distal end may be configured to be inserted into a urethra to evacuate a bladder.

In some embodiments, the catheter may be a male catheter.

In some embodiments, the catheter may be a female catheter.

In some embodiments, the kit may include a catheter assembly having a urinary catheter and a catheter case, the urinary catheter may have a distal end configured to be inserted into a urethra to evacuate a bladder, a proximal end, and a length between the distal end and the proximal end, the catheter case may include a top and a bottom joined together to provide the catheter case with a length and a width, an opening through the top for removal and/or re-insertion of the urinary catheter from and into the catheter case, and a guiding element disposed in at least one of the top and the bottom, the guiding element may be configured to maintain at least a portion of the urinary catheter in a curved configuration until use, and the guiding element may be configured to control the path of the urinary catheter during removal and re-insertion of the urinary catheter from and into the catheter case.

In some embodiments, the kit may include a catheter assembly having a catheter tube and a locator tip, the catheter tube may have a distal tip with a catheter tube distal opening to be inserted into a urethra of a female subject and a proximal tip having at least one catheter tube proximal opening, the locator tip may be located proximal the distal tip of the catheter tube, and the locator tip may be sized to remain outside a female urethra and configured to allow the catheter tube to pass therethrough.

According to yet another aspect of the present disclosure, a method of collecting urine may include connecting a first end of a catheter to any urine collection bag disclosed herein, inserting a second end of the catheter into the urethra, collecting urine into the urine collection bag through the catheter, removing the catheter from the urine collection bag, and threading the elongated portion of the urine collection bag through an aperture of the urine collection bag.

In some embodiments, the method may include tearing the urine collection bag at a perforation and draining the urine into a receptacle.

According to yet another aspect of the present disclosure still, a method of manufacturing a urine collection bag may include welding a first external layer to a first internal layer to generate a first assembly, welding a second external layer to a second internal layer to generate a second assembly, welding the first assembly to the second assembly to generate a combined assembly, and cutting the combined assembly to generate the urine collection bag.

In some embodiments, welding the first external layer to the first internal layer and welding the second external layer to the second internal layer may be performed concurrently.

In some embodiments, welding includes the use of heat and pressure.

In some embodiments, an apparatus including a welding tool and a cutting tool may be utilized for the welding and the cutting, respectively.

In some embodiments, the apparatus may be a single entity.

In some embodiments, the first external layer and/or the second external layer may include polyvinyl chloride.

In some embodiments, the first internal layer and/or the second internal layer may include polyvinyl chloride.

In some embodiments, the first external layer and/or the second external layer may have a thickness of about 75 microns to about 225 microns.

In some embodiments, the first internal layer and/or the second internal layer may have a thickness of about 75 microns to about 225 microns.

In some embodiments, the urine collection bag may include at least four sides, and not one of the at least four sides may be parallel to another one of the at least four sides.

These and other features of the present disclosure will become more apparent from the following description of the illustrative embodiments.

BRIEF DESCRIPTION OF THE DRAWINGS

The invention described herein is illustrated by way of example and not by way of limitation in the accompanying figures. For simplicity and clarity of illustration, elements illustrated in the figures are not necessarily drawn to scale. For example, the dimensions of some elements may be exaggerated relative to other elements for clarity. Further, where considered appropriate, reference labels have been repeated among the figures to indicate corresponding or analogous elements.

DETAILED DESCRIPTION

Figure 1:
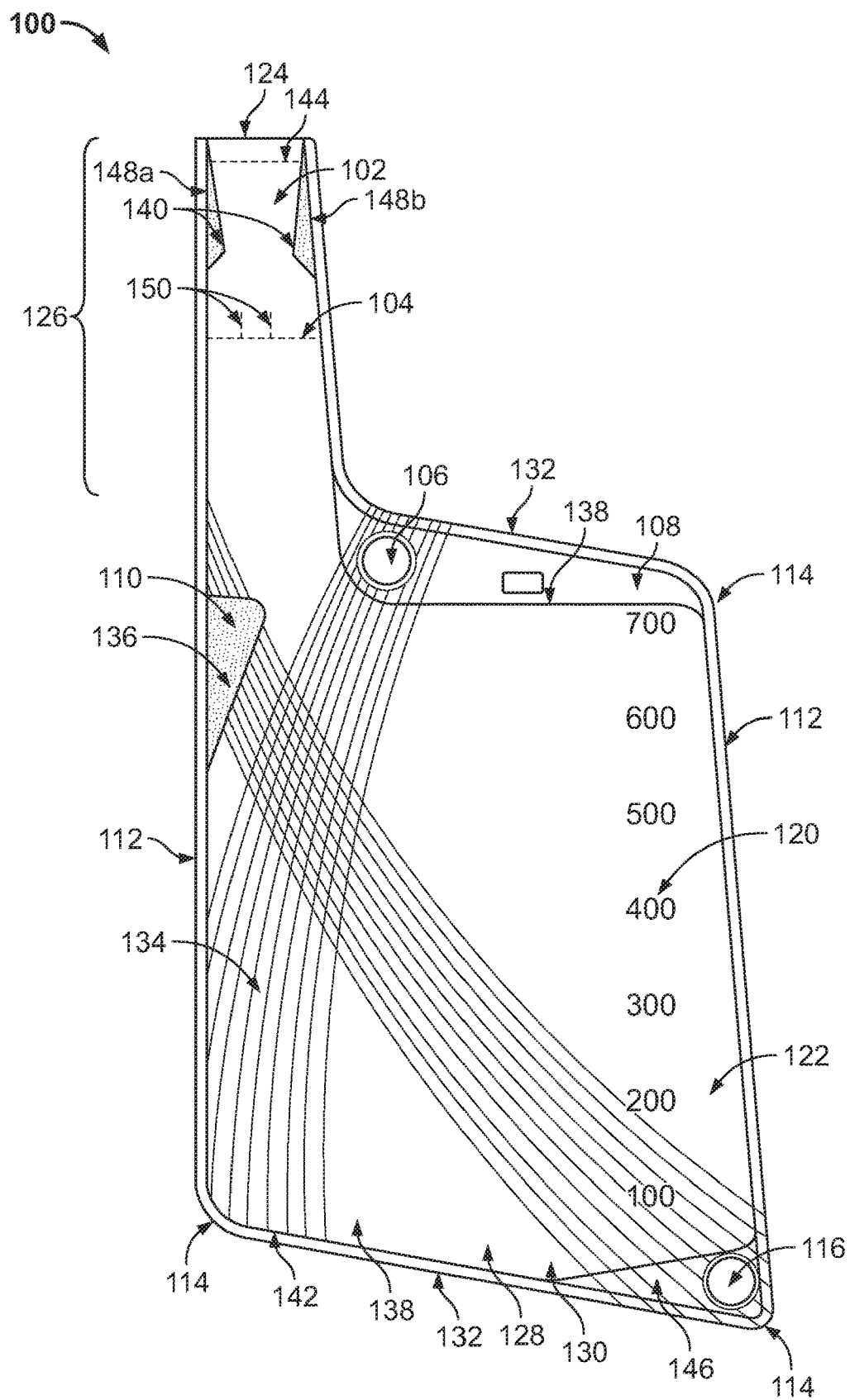
FIG. 1 illustrates an elevation view of one embodiment of a urine collection bag.

While the concepts of the present disclosure are susceptible to various modifications and alternative forms, specific embodiments thereof have been shown by way of example in the drawings and will be described herein in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described. Additionally, it should be appreciated that items included in a list in the form of "at least one A, B, and C" can mean (A); (B); (C); (A and B); (A and C); (B and C); or (A, B, and C). Similarly, items listed in the form of "at least one of A, B, or C" can mean (A); (B); (C); (A and B); (A and C); (B and C); or (A, B, and C).

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, may not be included or may be combined with other features.

A number of features described below may be illustrated in the drawings in phantom. Depiction of certain features in phantom is intended to convey that those features may be hidden or present in one or more embodiments, while not necessarily present in other embodiments. Additionally, in the one or more embodiments in which those features may be present, illustration of the features in phantom is intended to convey that the features may have location(s) and/or position(s) different from the locations(s) and/or position(s) shown.

The apparatus and features thereof shown in the figures are for illustrative purposes only and it is intended that urine collection bags of the present disclosure may include additional features and/or lack one or more features shown. For example, one or more of the following features may not be present in one or more urine collection bag embodiments of the present disclosure: perforation(s), graphic element(s), webbing section(s), valve(s), or aperture(s).

In one aspect of the present disclosure, urine collection bags include an outer profile and an inner profile that has a container portion for holding urine and an elongated portion for connecting to a catheter. In some cases, the elongated portion is capable of receiving a male catheter or other urinary catheter(s) designed for insertion into, and collection from, a male urethra. In other cases, the elongated portion is capable of receiving a female catheter or other urinary catheter(s) designed for insertion into, and collection from, a female urethra.

In exemplary embodiments, the urine collection bag, including the catheter connection portion, includes a non-rigid material. That construction may allow the urine collection bag to fold to a generally flat shape or profile to facilitate storage, enhance discreteness, and reduce weight. In some embodiments, the urine collection bag includes one or more features to prevent or reduce leakage of urine. In one example, the urine collection bag includes a one-way valve positioned within the catheter connection portion. In some embodiments, the valve may be a one-way valve. Additionally, in some embodiments, the valve may be flexible or non-rigid. In other embodiments still, the catheter connection portion may attach to a urinary catheter via a luer-lock member or the like.

In another example, the urine collection bag may be configured with an aperture and at least a portion of the elongated portion may be threadable through the aperture to secure the collected urine. Such threading may be easier for some users who cannot perform alternative securing methods, such as tying the elongated portion into a knot, for instance. However, in situations where tying a knot is desired, the catheter connection portion may be elongated to allow a user to tie a knot in the area of the elongated portion. In any case, the present disclosure also provides urinary catheter systems including a urine collection bag and a catheter, methods of collecting urine using urinary catheter systems, and methods of manufacturing urine collection bags.

Urine Collection Bag

A non-limiting example of a urine collection bag 100 is shown in FIG. 1. The collection bag 100 includes a first external layer 128 and a second external layer 130 sealed around a first periphery 138 to define an inner profile. The inner profile has a container portion 122 for holding fluid and an elongated portion 126 that has an opening 124 and a connection portion 102 for receiving a catheter through the opening 124. The first external layer 128 and the second external layer 130 are also sealed around a second periphery 132 to define an outer profile surrounding the inner profile. In some embodiments, the first external layer 128 and the second external layer 130 may be sealed together by welding.

Collection Bag Profile

In general, urine collection bags have a curved outer profile to minimize discomfort associated with rough edges. However, when such bags are placed horizontally on a flat surface and filled with urine, they may bulge and pinch such that movement of the bags may be unpredictable. In some embodiments, the urine collection bag 100 has an overall flat shape that may serve to control the center of gravity of the filled collection bag 100 when the bag 100 lies horizontally or in a vertical position (e.g., when the collection bag 100 is hung). That shape may provide the user with a predictable and controllable mass before, during, and after use. The user may safely place the collection bag 100 on a flat surface while filled substantially without spilling, rolling, and/or moving unpredictably. As a result, the user may fill the collection bag 100 while disposed in a seated or lying position in a controlled fashion, which may reduce unpredictable movement from the collection bag 100 and the likelihood of leakage at the connection point with the catheter.

In one aspect, the outer and inner profiles of the urine collection bag 100 include one or more sides 112 that are at least substantially straight. In some embodiments, at least one of the sides 112 is not parallel to another side 112 of the collection bag 100. Additionally, in some embodiments, the substantially straight sides 112 provide a more controlled form as the collection bag 100 fills, thereby avoiding pinching and bulging that may occur with other configurations (e.g., curved sides). The substantially straight sides 112 may allow the collection bag 100 to fill to a relatively constant thickness to provide a flat profile from the side. Consequently, the sides may facilitate reduction of peak pressure points and, in turn, reduce the likelihood of bursting or perforation due to a relatively even distribution of force or pressure.

In some embodiments, a urine collection bag may include two, three, four, five, or six substantially straight sides. Additionally, in some embodiments, a substantially straight side may have a length of at least about 1 cm and a curvature of less than about two degrees. In some embodiments still, a substantially straight side may have a length of at least about 5 cm and a curvature of less than about two degrees. Furthermore, in some embodiments, the length of one or more sides may be from about 1 cm to about 20 cm, from about 1 cm to about 15 cm, from about 3 cm to about 20 cm, from about 3 cm to about 15 cm, from about 5 cm to about 20 cm, or from about 5 cm to about 15 cm. Further still, in some embodiments, at least one of the sides may have a length that is at least about 10% of the longest length of the bag. As non-limiting examples, the length of at least one of the substantially straight sides may be about or at least about 10%, 20%, 30%, 40%, 50%, 60%, 70%, 80%, 90%, or 100% of the longest length of the bag.

In some embodiments, the urine collection bag 100 includes one or more corners 114 each having an angle of at least about 90° to at least about 160, at least about 95° to at least about 150, at least about 100° to at least about 140, at least about 110° to at least about 130, at least about 115 to at least about 125, or at least about 120° to at least about 125. In other embodiments, the angle of each of the corners 114 may be about 90°, about 95°, about 100, about 105, about 110, about 115, about 120, about 125, about 130, about 135, about 140, about 145, about 150, about 155, or about 160. Additionally, in some embodiments, at least two of the one or more corners 114 may share the same angle. In other embodiments, however, each of the one or more corners 114 may have a different angle.

In some embodiments, the corners 114 may have a radius from about 3/32 inch to about 3/4 inch. For example, the urine collection bag 100 may include two, three, four, five, or six corners that each include, or otherwise define, at least one radius. The radii of the corners may reduce peak pressures that form around or near the corners when the collection bag is filled to reduce bulging of the collection bag.

In some embodiments, a urinary collection bag may include a folded bottom. In such embodiments, the base of the container portion may be folded internally so that as the bag is filled, it blossoms to form a reliable, wider base. In some cases, the bag may be capable of standing upright when filled to at least about 10%, 20%, 30%, 40%, 50%, 60%, 70%, or 80% capacity.

External Layers and Bag Materials

In some embodiments, the first external layer 128 and the second external layer 130 each include a non-rigid material. The material properties of the selected non-rigid material allow facilitate compact storage of the unused urine collection bag 100 by allowing the bag 100 to be folded flat. Additionally, the material properties of the layers 128, 130 also lend to discreteness by minimizing emitted noise upon unfolding, as well as during use of the bag 100. In some embodiments, the first external layer 128 and/or the second external layer 130 have a roughness of about 0.5 micron to about 3 micron, or about 1 micron to about 2.5 micron. It should be appreciated that roughness may be measured by a TM-500, TM-553, or Papyro-Tex Instr. I KO 13. Additionally, in some embodiments, the first external layer 128 and/or the second external layer 130 have a tensile strength of at least about 10 MPa, at least about 12 MPa, at least about 15 MPa, or about 10 MPa to about 60 MPa. Furthermore, in some embodiments, the first external layer 128 and/or the second external layer 130 have an elongation at break of at least about 150%, at least about 165%, at least about 175%, or about 150% to about 700%. The elongation break may be measured by ISO 527-1 and/or ISO 527-3, at least in some embodiments.

In some embodiments, the first external layer 128 and/or the second external layer 130 have an extended tear strength of at least about 70 N/mm, at least about 80 N/mm, at least about 90 N/mm, about 70 N/mm to about 110 N/mm, about 70 N/mm to about 100 N/mm, about 80 N/mm to about 110 N/mm, or about 80 N/mm to about 100 N/mm. The extended tear strength may be measured according to DIN 53363: 2003-10, at least in some embodiments. In some embodiments, the first external layer 128 and/or second external layer 130 have a thickness of less than or equal to about 200 microns, 180 microns, 160 microns, 140 microns, 120 microns, 100 microns, 80 microns, or 50 microns. Additionally, in some embodiments, the first external layer 128 and/or second external layer 130 have a thickness of about 75 microns to about 225 microns, about 100 micron to about 200 microns, about 75 microns to about 125 microns, about 85 microns to about 115 microns, or about 75 microns, about 80 microns, about 85 microns, about 90 microns, about 95 microns, about 100 microns, about 105 microns, about 110 microns, about 115 microns, about 120 microns, or about 125 microns.

In some embodiments, the first external layer 128 and/or the second external layer 130 include polyvinyl chloride, polypropylene, polyethylene, ethylene-vinyl acetate, or a combination thereof. In one example, the first external layer 128 and/or second external layer 130 include polyvinyl chloride. Additionally, in some embodiments, the first external layer 128 and/or the second external layer 130 include a plasticiser. Non-limiting examples of plasticisers include di(2-ethylhexyl) terephthalate (DEHT) and an epoxidised plasticiser. Further, in some embodiments still, the first external layer 128 and/or the second external layer 130 include a stabiliser. Non-limiting examples of stabilisers include barium and zinc.

In some embodiments, the first external layer 128 and/or the second external layer 130 do not include a phthalate. Additionally, in some embodiments, the first external layer 128 and/or the second external layer 130 do not include natural rubber latex. In some embodiments still, the first external layer 128 and/or the second external layer 130 do not include di(2-ethylhexyl) phthalate (DEHP). In some embodiments yet still, the first external layer 128 and/or the second external layer 130 are transparent. In an exemplary embodiment, the first external layer 128 and the second external layer 130 each do not include a phthalate, each include polyvinyl chloride (PVC), each have a thickness of about 100 microns, and each include transparent material.

In some embodiments, the first external layer 128 and/or second external layer 130 include a graphic element. The graphic element may have one or more features that align with certain user interaction points, at least in some embodiments. The graphic element(s) may also provide indications of the services that are afforded to the user and a branding element. In some embodiments, a graphic element includes a scale 120. When the collection bag 100 is positioned vertically or held by a first aperture 106, the scale 120 provides an approximate indication of the volume of collected fluid. Additionally, in some embodiments, a graphic element includes arches 134 that align with certain user interaction points, such as the first aperture 106, a second aperture 116, and a perforated tear line 110.

Interface Between Inner and Outer Profiles

In some embodiments, positioned between the inner profile and the outer profile are one or more webbing sections. The urine collection bag 100 shown in FIG. 1 includes a first webbing section 108, a second webbing section 146, a third webbing section 136, and fourth webbing sections 148a and 148b. The one or more webbing sections may provide strength to the form of the collection bag 100 during urine collection and drainage. In some cases, the boundaries of a webbing section are formed by welding together at least the first external layer 128 and the second external layer 130. In any case, the first webbing section 108 includes the first aperture 106. The first aperture 106 may be used as a rotationally compatible grip for holding and positioning the urine collection bag 100 prior to, during, and after use (e.g., during drainage of the collected urine). The first aperture 106 may also be used to hang the urine collection bag 100. After urine collection, at least a portion of the elongated portion 126 may be threaded through the first aperture 106 to prevent leakage of urine from the opening 124. As such, the size of the first aperture 106 may be large enough to allow the elongated portion 126 to be threaded through, yet tight enough to apply some resistance to the elongated portion 126. The threading process may be easier for a user than tying a knot in the elongated portion 126. The second webbing section 146 includes the second aperture 116, which may also be used to hold and/or hang the urine collection bag 100 in a similar manner as described above for the first aperture 106.

At least in some embodiments, the collection bag 100 includes the perforated tear line 110. The perforated tear line 110 is at least partially positioned within the third webbing section 136, which may allow for a more controlled tearing than if the perforated tear line 110 were positioned entirely within the separated first external layer 128 and the second external layer 130. In some embodiments, after urine collection, a user may tear along the perforated tear line 110 to substantially separate the elongated portion 126 from the container portion 122 and pour out the collected urine. The perforated tear line 110 may be positioned such that after the elongated portion 126 is threaded through the first aperture 106, a user may still open the collection bag 100 at the perforated tear line 110 to remove the collected urine.

Elongated Portion

The elongated portion 126 of the urine collection bag 100 includes a connection portion 102 for connecting the collection bag 100 to a male and/or a female catheter, at least in some embodiments. In some embodiments, the catheter may establish a friction fit connection with the connection portion 102. The connection portion 102 has a tapered profile that provides an increasingly tight fit with the catheter end to allow a user to push the two interfacing parts together and subsequently pull the two parts apart to break the connection and remove the catheter. In the embodiment shown in FIG. 1, the internal tapered profile is formed with welds 140. The connection portion 102 is non-rigid to allow the collection bag 100 to fold to a more compact form than if the connection portion 102 had a rigid construction. In some embodiments, the connection portion 102 has a hardness of less than about 60 Shore A.

In some embodiments, the connection portion 102 includes a notch 144 that is located at the opening 124 to facilitate insertion of the catheter into the connection portion 102. The notch 144 may be formed by having a first external layer 128 that is shorter than the second external layer 130 at the connection portion 102, or vice versa.

The elongated portion 126 of the collection bag 100 includes a one-way valve 104 that has a first internal layer and a second internal layer which cooperatively allow urine to flow in one direction into the container portion 122, and which close under pressure to prevent or reduce urine flow in the opposite direction. In some embodiments, the valve 104 may be formed by welding together the first internal layer, the second internal layer, the first external layer 128, and the second external layer 130. Additionally, in some embodiments, the first and/or second internal layer include a weld 150.

In some embodiments, the first internal layer and the second internal layer each include a non-rigid material. Additionally, in some embodiments, the first internal layer and/or the second internal layer have a roughness of about 0.5 micron to about 3 micron, or about 1 micron to about 2.5 micron. Roughness may be measured by a TM-500, a TM-553, or a Papyro-Tex Instr. I KO 13. Furthermore, in some embodiments, the first internal layer and/or the second internal layer have a tensile strength of at least about 10 MPa, at least about 12 MPa, or at least about 15 MPa. Further still, in some embodiments, the first internal layer and/or the second internal layer have an elongation at break of at least about 150%, at least about 165%, or at least about 175%. The elongation break may be measured by ISO 527-1 and/or ISO 527-3. Further yet still, in some embodiments, the first internal layer and/or the second internal layer have an extended tear strength of at least about 70 N/mm, at least about 80 N/mm, or at least about 90 N/mm. The extended tear strength may be measured according to DIN 53363: 2003-10.

In some embodiments, the first internal layer and/or the second internal layer have a thickness of less than or equal to about 200 microns, 180 microns, 160 microns, 140 microns, 120 microns, 100 microns, 80 microns, or 50 microns. Additionally, in some embodiments, the first internal layer and/or the second internal layer have a thickness of about 75 microns to about 225 microns, about 100 micron to about 200 microns, about 75 microns to about 125 microns, about 85 microns to about 115 microns, or a thickness of about 75 microns, about 80 microns, about 85 microns, about 90 microns, about 95 microns, about 100 microns, about 105 microns, about 110 microns, about 115 microns, about 120 microns, or about 125 microns.

In some embodiments, the first internal layer and/or the second internal layer include polyvinyl chloride, polypropylene, polyethylene, ethylene-vinyl acetate, or a combination thereof. In one such embodiment, the first internal layer and/or the second internal layer include polyvinyl chloride. Additionally, in some embodiments, the first internal layer and/or the second internal layer include a plasticiser. Non-limiting examples of plasticisers include di(2-ethylhexyl) terephthalate (DEHT) and an epoxidised plasticiser. Furthermore, in some embodiments, the first internal layer and/or the second internal layer include a stabilizer. Non-limiting examples of stabilisers include barium and zinc.

In some embodiments, the first internal layer and/or the second internal layer do not include a phthalate. Additionally, in some embodiments, the first internal layer and/or the second internal layer do not include natural rubber latex. In some embodiments still, the first internal layer and/or the second internal layer do not include di(2-ethylhexyl) phthalate (DEHP). In some cases, the first internal layer and/or the second internal layer are transparent. In an exemplary embodiment, the first internal layer and the second internal layer of the valve 104 do not include a phthalate, include polyvinyl chloride (PVC), have a thickness of about 100 microns, and include transparent material.

In some embodiments, the length of the elongated portion 126 is at least about 60 mm, at least about 70 mm, at least about 80 mm, at least about 90 mm, at least about 100 mm, at least about 110 mm, at least about 120 mm, at least about 130 mm, at least about 140 mm, or at least about 150 mm. Additionally, in some embodiments, in order to provide sufficient length for threading through the hole 106 to resist leakage of the contents of the bag 100, the length of the elongated portion 126 is between about 60 mm to about 100 mm, between about 70 mm to about 90 mm, or between about 75 mm to about 85 mm. In other embodiments, where tying a knot into the elongated portion 126 is desired, for example, the length of the elongated portion 126 may be longer than 150 mm.

Container Portion

In some embodiments, the container portion 122 is configured to hold between about 200 mL and about 1000 mL of fluid. Additionally, in some embodiments, the container portion 122 is configured to hold about 50-1500 mL, 50-1400 mL, 50-1300 mL, 50-1200 mL, 50-1100 mL, 50-1000 mL, 50-900 mL, 50-800 mL, 100-1500 mL, 100-1400 mL, 100-1300 mL, 100-1200 mL, 100-1100 mL, 100-1000 mL, 100-900 mL, 100-800 mL, 200-1500 mL, 200-1400 mL, 200-1300 mL, 200-1200 mL, 200-1100 mL, 200-1000 mL, 200-900 mL, or 200-800 mL of liquid. Furthermore, in some embodiments, the container portion 122 is configured to hold about 200 mL, 300 mL, 400 mL, 500 mL, 600 mL, 700 mL, 800 mL, 900 mL, 1000 mL, 1100 mL, or 1200 mL of liquid.

Urinary Catheter Systems

In another aspect of the present disclosure, systems including any urine collection bag described herein and one or more accessory components are contemplated. Accessory components include, but are not limited to, catheters and components for use with a catheter system. In some embodiments, the urine collection bag includes an outer profile, an inner profile, and first and second external layers sealed around a first periphery to define the inner profile. In such embodiments, the inner profile includes a container portion for holding fluid and an elongated portion capable of receiving a catheter through an opening thereof.

In some cases, the elongated portion is capable of receiving a male catheter. As a non-limiting example, the male catheter may be the catheter disclosed in International Application No. PCT/US18/67363, which was filed on Dec. 21, 2018, or any other male urinary catheter(s) similar to the male catheter disclosed in International Application No. PCT/US18/67363 that is designed for insertion into, and collection from, a male urethra. In other cases, the elongated portion is capable of receiving a female catheter. As a non-limiting example, the female catheter may be the catheter disclosed in International Application No. PCT/US18/67366, which was filed on Dec. 21, 2018, or other urinary catheter(s) similar to the female urinary catheter disclosed in International Application No. PCT/US18/67366 that is designed for insertion into, and collection from, a female urethra. The aforementioned disclosures are incorporated by reference herein in their entireties.

Male Catheters

In some embodiments, an accessory includes a male catheter and/or a male catheter assembly. Exemplary male catheters and assemblies are disclosed in International Application No. PCT/US18/67363. In some embodiments, the urinary catheter assembly includes (i) a urinary catheter having a distal end configured to be inserted into a urethra to evacuate a bladder, a proximal end, and a length therebetween, and (ii) a catheter case. In some embodiments, the catheter case includes a top and a bottom joined together to provide the catheter case with a length and a width, an opening through the top for removal and/or re-insertion of the urinary catheter from and into the catheter case, and a guiding element disposed in at least one of the top and the bottom. Additionally, in some embodiments, the guiding element is configured to maintain at least a portion of the urinary catheter in a curved configuration until use, and the guiding element is configured to control the path of the urinary catheter during removal and re-insertion of the urinary catheter from and into the catheter case.

In some embodiments, at least a portion of the curved configuration of the urinary catheter has an "S" shape. Additionally, in some embodiments, at least a portion of the curved configuration of the urinary catheter has an "8" shape. In some embodiments still, the curved configuration of the urinary catheter does not include more than two turns. Further, in some embodiments, a region of the urinary catheter most proximal to the distal end thereof is straight. In some embodiments yet still, the region is about 5 cm to about 15 cm in length. Finally, in some embodiments, the guiding element is a bearing in a configuration that is the same as at least a portion of the curved configuration.

In some embodiments, the urinary catheter assemblies of the present disclosure include a lid to provide access to the opening 124. Additionally, in some embodiments, the lid is configured to close the opening 124 to provide a fluid tight seal to the catheter case. Furthermore, in some embodiments, the lid is connected to the top of the catheter case by a hinge. In such embodiments, the hinge may be offset clockwise or counter-clockwise relative to a center line or axis of the assembly. For example, the hinge may be offset from the center line or axis by at least 15 degrees, by at least 30 degrees, by at least 45 degrees, by at least 60 degrees, by at least 75 degrees, or by at least 90 degrees, at least in some embodiments.

In some embodiments, a urinary catheter assembly of the present disclosure includes a hollow funnel connected to the proximal end that is configured to be held while the distal end is inserted into the urethra. Additionally, in some embodiments, the hollow funnel has a substantially circular configuration at the proximal end and tapers to a flattened, substantially oval configuration at an opposite end that forms a spout. Furthermore, in some embodiments, the hollow funnel has a substantially circular configuration at the proximal end and a substantially circular configuration at an opposite end that forms a spout. In one example, the spout end of the hollow funnel has semi-major and semi-minor axes that are substantially equal. In some embodiments still, the urinary catheter assembly includes an expandable sleeve disposed around the catheter that has a first sleeve end connected to the funnel and a second sleeve end disposed away from the funnel. In those embodiments, the expandable sleeve may be compressed in an unexpanded state prior to use of the urinary catheter. In some embodiments yet still, the urinary catheter assembly includes a slidable gripper disposed around the catheter that has a first gripper end connected to the second sleeve end and a free second gripper end.

In some embodiments, the urinary catheter assembly of the present disclosure includes a wetting device having a front and a back that form a volume therebetween and that each has an opening disposed and configured to allow the catheter to pass therethrough. Additionally, in some embodiments, the urinary catheter assembly includes a wetting applicator having a liquid absorbed therein that is disposed in the volume. In such embodiments, the wetting applicator has an opening that extends therethrough and is configured to supply the liquid to a surface of the urinary catheter as the urinary catheter passes through the openings in the front and the back of the wetting device. In some embodiments, the wetting device is disposed adjacent the free gripper end of the slidable gripper to maintain compression of the expandable sleeve in an unexpanded state prior to use. In some embodiments still, the opening in the wetting applicator is smaller than the openings in the front and the back of the wetting device. Further, in some embodiments, prior to use, the hollow funnel passes through the opening in the wetting applicator and through the openings in the front and the back of the wetting device to provide a fluid tight seal to the wetting device.

In some embodiments, the urinary catheter assembly of the present disclosure includes an O-ring. The O-ring may be located between the top and bottom outer edges to provide a seal that maintains sterility of the catheter tube until use, at least in some embodiments. Additionally, in some embodiments, the urinary catheter assembly includes an O-ring located between the top and bottom inner edges of a handle in the catheter case.

In some embodiments, to maintain sterility of the catheter assemblies, the top and bottom outer edges of the assemblies may be sealed using laser welding. Once welded, the resultant seal maintains sterility of the catheter tube until use. Additionally, in some embodiments, subsequent to welding, the resultant seal maintains a sterile barrier after sterilization of the urinary catheter assembly. It should be appreciated that in such embodiments, the materials used in conjunction with laser welding may be selected to allow a laser to pass through the assembly region in the vicinity of where one or more laser welds are required. The laser frequency may be a diode laser configured for operation at from 850 to 1100 nm wavelength, from 900 to 1050 nm wavelength, from 960 to 1010 nm wavelength, or at 980 nm wavelength, at least in some embodiments.

In one example, if the catheter assembly is sealed using laser welding, the top of the catheter case may be laser absorbing and the bottom of the case may be laser translucent. In another example, if the catheter assembly is sealed using laser welding, the bottom of the catheter case may be laser absorbing and the top of the case may be laser translucent. Materials that are capable of allowing a laser to pass through in order to establish a laser weld and achieve sterility include, but are not limited to, laser transparent or laser translucent plastic or resin, such as a polypropylene (PP) containing an organic pigment, a polyphenylene ether (PPE) containing an organic pigment, a polycarbonate (PC) containing an organic pigment, or an acrylonitrile butadiene styrene (ABS) containing an organic pigment, for example. In some embodiments, the laser may pass through a laser translucent plastic. Additionally, in some embodiments, the material that allows a laser to pass through may also include reduced amounts of (or zero) black or laser absorbing pigment (e.g., iron oxide or carbon black). The removal of black or laser absorbing pigment may reduce the amount of laser energy absorbed by the material, thereby allowing increased energy to pass through the assembly region being laser welded.

In some embodiments of a laser absorbing catheter case, the top and/or bottom may include plastic or resin. The plastic or resin may include a polypropylene (PP) containing an inorganic pigment (e.g., iron oxide) or carbon black, a polyphenylene ether (PPE) containing an inorganic pigment or carbon black, a polycarbonate (PC) containing an organic pigment or carbon black, or an acrylonitrile butadiene styrene (ABS) containing the organic pigment or carbon black, for example. Typically, the urinary catheter assembly may be sterilized after manufacture by exposure to e-beam or gamma radiation. Sterilization may typically occur when the urinary catheter assembly is packaged and ready for shipment.

In some embodiments, the urinary catheter includes, or is integrated with, a polymer, such as a hydrophilic polymer, for example. Additionally, in some embodiments, the urinary catheter is coated with a polymer, such as a hydrophilic polymer, for instance. In some embodiments still, the urinary catheter includes or is integrated with a polymer mixture of a thermoplastic or thermo-curing polymer base material and an amphiphilic block copolymer (e.g., as disclosed in WIPO Publication No. 2011/051439, which was filed on Oct. 29, 2010 and which is incorporated by reference herein in its entirety). Further, in some embodiments, the urinary catheter is coated with the polymer mixture of a thermoplastic or thermo-curing polymer base material and amphiphilic block copolymer (e.g., as disclosed in the aforementioned WIPO publication).

In some embodiments, an accessory of the present disclosure includes a catheter case for storing and dispensing a urinary catheter and a wetting device. In such embodiments, the catheter case includes a top and a bottom joined together to provide the catheter case with a length and a width, an opening through the top for removal and/or re-insertion of the urinary catheter from and into the catheter case, and a guiding element disposed in at least one of the top and the bottom. At least in some embodiments, the guiding element is configured to maintain at least a portion of the urinary catheter in a curved configuration until use, and the guiding element is configured to control the path of the urinary catheter during removal and re-insertion of the urinary catheter from and into the catheter case. In some embodiments, catheter cases disclosed herein include a lid configured to close the opening 124 to provide a fluid tight seal to the catheter case as discussed above.

In some embodiments, the lid includes a tab connected to the lid by a joint. In such embodiments, the tab may be configured to be bent away from the catheter case to create a grip to open the lid. Additionally, in some embodiments, bending of the tab may create a fatigue mark in the joint that provides a visible tamper-evident indication. In some embodiments still, the lid includes a first engaging member that interacts with a second engaging member of the top of the catheter case. The first and/or second engaging members may include a bump, a clip, a notch, or any protrusion or depression configured to interact with the other engaging member to close the catheter lid. In an exemplary embodiment, after re-insertion of the urinary catheter into the catheter case, the lid is closed by pressing the first engaging member of the lid against the top of the catheter case to enclose the urinary catheter within the catheter case. It should be appreciated that in some embodiments, minimal or substantially no liquid from the catheter is released from the catheter case when the lid is closed. Furthermore, in some embodiments, the tab is connected to the catheter case using an ultrasonic weld, and in such embodiments, moving the tab away from the catheter case irreversibly and noticeably damages the ultrasonic weld to provide a visible tamper-evident indication.

In some embodiments, the catheter case includes a seal that covers the opening 124 and a connecting tab disposed on an upper surface of the seal that is adhered to an underside of lid so that the seal is peeled open as the lid is opened, thereby providing a visible tamper-evident indication. In other embodiments, the catheter case includes a seal that covers the opening 124 and does not include a connecting tab. In such embodiments, a user may manually have to open the seal separately from the lid, and the seal continues to provide a visible tamper-evident indication. In some embodiments still, the lid and the top may include mating elements, such as a clip feature on the lid and a notch feature on the top, for example, that cooperatively provide a labyrinthine pathway to resist egress of liquid droplets from a closed or re-closed catheter case. In some embodiments yet still, the lid may be sealed using an exterior paper-type seal that is placed on either the exterior top or bottom face of the assembly. In one example, the lid may be sealed using an overlapping top and bottom face of the assembly which clicks into place to lock the top and bottom faces of the assembly together.

In some embodiments, as mentioned above, the catheter case may include a labyrinthine pathway to prevent egress of liquid droplets from the closed or re-closed case after use of the urinary catheter. The labyrinthine pathway may be formed by a plurality of protrusions projecting from the lid toward the opening. Additionally, in some embodiments, one of the plurality of protrusions may contact the seal and another of the plurality of protrusions may project into a channel adjacent the opening. In some embodiments still, at least a portion of the guiding element may form a generally "S"-shaped curved configuration. In some embodiments yet still, the guiding element may cross itself no more than once and reverse direction no more than twice. Furthermore, in some embodiments, the top and the bottom of the case each have a generally oval shape, and the opening has a generally circular shape. Further still, in some embodiments, the guiding element may include a first plurality of ribs disposed in each of the top and the bottom of the case that substantially match each other.

In some embodiments, a catheter case of the present disclosure may include a wetting device having a front and a back that form a volume therebetween, and each of the front and the back has an opening disposed and configured to allow the catheter to pass therethrough. Additionally, in some embodiments, catheter cases of the present disclosure include a retaining element disposed in at least one of the top and the bottom and configured to retain the wetting device. In some embodiments still, the retaining element may include a second plurality of ribs disposed in each of the top and the bottom of the case that substantially match each other.

It should be noted that as used herein, the terms "first", "second", "third", "upper", "lower", "top" and "bottom" and the like denote and/or modify various elements. However, these terms do not imply a spatial, sequential, or hierarchical order unless specifically stated.

Female Catheters

In some embodiments, an accessory of the present disclosure includes a female catheter and/or catheter assembly. An exemplary female catheter is disclosed in International Application No. PCT/US18/67366. In some embodiments, the catheter assembly includes (i) a catheter tube having a distal tip with a catheter tube distal opening that is adapted for insertion into a urethra of a female subject and a proximal tip having at least one catheter tube proximal opening, and (ii) a locator tip located proximal the distal tip of the catheter tube. Additionally, in some embodiments, the locator tip is sized to remain outside a female urethra and configured to allow the catheter tube to pass through the locator tip.

In some embodiments, the locator tip appears conical from a side view of the catheter assembly. In other embodiments, however, the locator tip appears rounded from a side view of the catheter assembly. In some embodiments still, the locator tip appears circular from an end view of the catheter assembly. In any case, in some embodiments, the locator tip is characterized by a height that is parallel with the length of the catheter tube and a width that is perpendicular to the length of the catheter tube when the catheter tube is extended. In one example, the width is not less than 2 cm. In another example, the width is not less than 1.5 cm. In yet another example, the width is not less than 1 cm. In another example still, the height is not greater than 1 cm.

In some embodiments, the catheter tube is located in a housing having an outer body and a cavity within the outer body. The housing includes a distal end proximate the locator tip and a proximal end. In some embodiments, catheter assemblies of the present disclosure have an actuator configured to be engaged by a user so that the actuator pushes the catheter tube out of the housing, through the locator tip, and into the urethra. Additionally, in some embodiments, the housing has a proximal opening at the proximal end that is configured to permit movement of the actuator therethrough. In some embodiments still, catheter assemblies disclosed herein include a sleeve configured to be held by the user as the urethra is being located. Furthermore, in some embodiments, catheter assemblies of the present disclosure include a cap configured to cover the locator tip until use. In such embodiments, the cap may also be configured to cover the catheter tube proximal opening after use. Finally, in some embodiments, the catheter tube includes a funnel on the proximal tip and the cap is also configured to cover the funnel after use.

In some embodiments, catheter assemblies of the present disclosure include a wetting device located behind the locator tip and configured to receive at least a portion of the catheter therethrough. Additionally, in some embodiments, catheter assemblies of the present disclosure include a sleeve connected to the locator tip. In some embodiments still, the sleeve is compacted prior to use. In some embodiments yet still, the sleeve and the locator tip are compacted in a proximal region of the catheter assembly prior to use.

In some embodiments, catheter assemblies disclosed herein include a case for storing the catheter assembly. Additionally, in some embodiments, the locator tip is engaged or connected to the case. Furthermore, in some embodiments, upon removal of the catheter assembly from the case, the sleeve is extended over the catheter tube. In some cases, the locator tip is disengaged from the case when the distal end of the catheter assembly is removed from the case. In some embodiments still, catheter assemblies disclosed herein include a wetting device. In some embodiments yet still, the catheter tube is wetted with a wetting agent upon removal of the catheter assembly.

Figure 2:
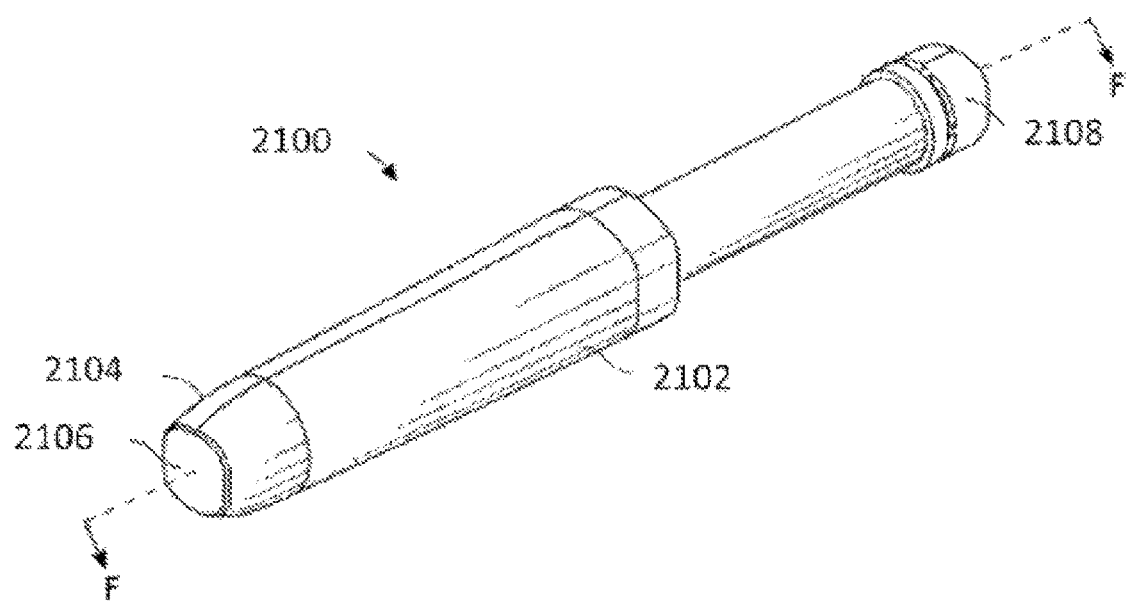
FIG. 2 illustrates a perspective view of one embodiment of a female urinary catheter.

Referring now to FIG. 2, catheter assemblies disclosed herein (e.g., the catheter assembly 2100) may be configured in, or otherwise housed by, a small, compact case. The case may generally have an outer body 2102 and a cap 2104 proximate the distal tip of the catheter tube. The case may have a distal end 2106 and a proximal end 2108 that is pushed in the direction of cap 2104 after the cap 2104 is removed in order to move the catheter tube through a locator tip near the distal tip of the catheter tube.

Figure 3:
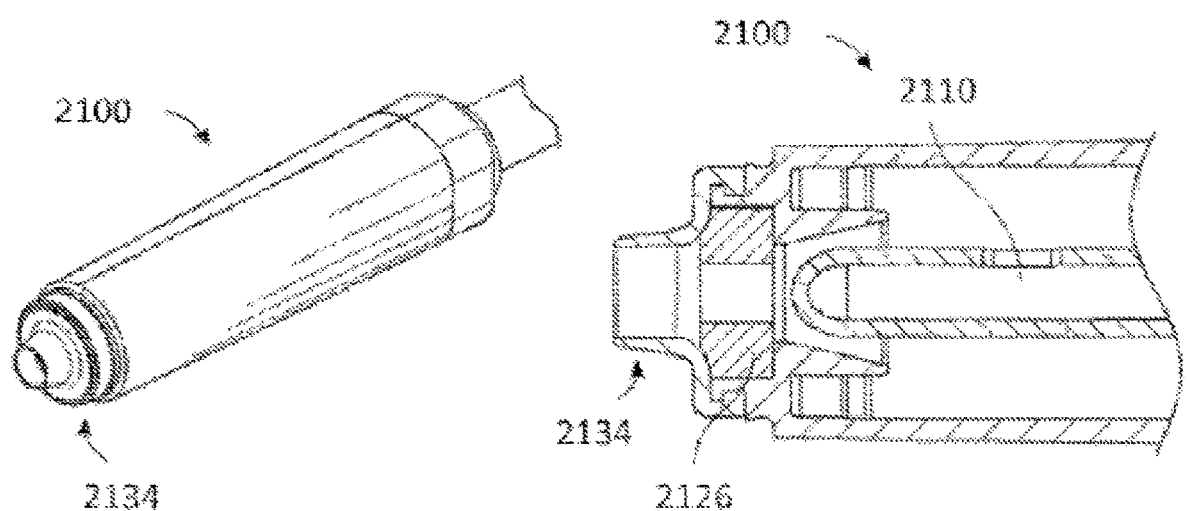
FIG. 3 illustrates a partial perspective view (i.e., on the left) and a cross-sectional view (i.e., on the right) of an exemplary female urinary catheter with a cap removed to expose a locator tip on the distal end thereof.

FIG. 3 depicts an outer view of a catheter assembly 2100 (i.e., on the left) and a cross-sectional side view of the catheter assembly 2100 (i.e., on the right). On the left, the catheter assembly 2100 is shown with a cap removed to expose a locator tip 2134. The locator tip 2134 may be described as tapered with a slope that may gradually increase toward the base of the locator tip 2134. The locator tip 2134 may be described as cone-shaped, at least in some embodiments. Although hollow, the locator tip 2134 may also be described as having a flat end and/or a blunt end. In any case, the end of the locator tip 2134 has a diameter that is smaller than the base of the locator tip 2134 which is attached to the device housing. On the right, the catheter tube 2110 is depicted as being protected from exposure by the locator tip 2134. In addition, in the illustrative embodiment, the catheter tube 2110 must be pushed through a wetting device 2126 and the locator tip 2134 before it may make contact with tissue.

Figure 4:
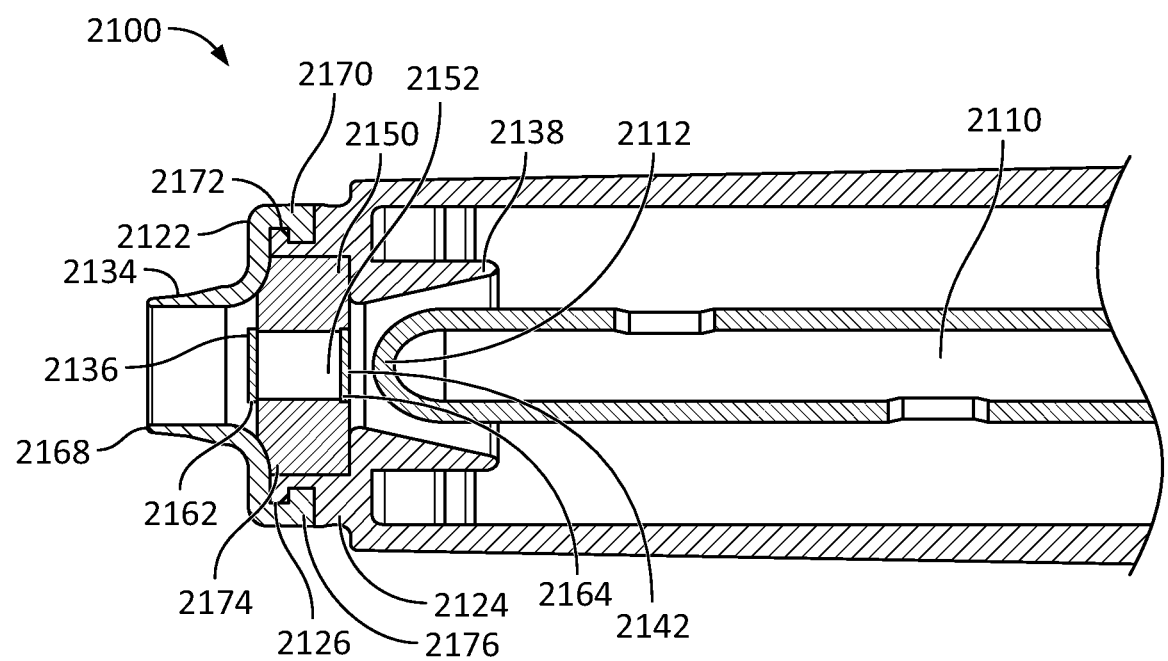
FIG. 4 illustrates a cross-sectional view of an exemplary female urinary catheter including a locator tip with a cap (not shown) removed.

FIG. 4 depicts an additional side view of a cross-section of the catheter assembly 2100 including a catheter tube 2110 having a distal tip 2112, an elongated portion 2138 that may guide the path of the catheter tube 2110, a wetting applicator 2150 with a connector 2152 extending therethrough, housing lips 2172, 2174, and locator tip rings 2170, 2176 that attach the locator tip 2134 to the housing. In some embodiments, the connector 2152 may have plugs 2162, 2164 to maintain a seal for the wetting agent in the wetting applicator 2150. The locator tip 2134 may have a tapered region near the locator tip opening 2168.

The wetting device 2126 may include a chamber formed by a rearward section 2124 and a forward section 2122 that includes the locator tip 2134. The wetting device 2126 may have an opening 2136 through the forward section 2122 and a housing opening 2142 through rearward section 2124. The openings 2136, 2142 may be disposed in concentric alignment with catheter tube 2110 so that the catheter can be pushed through the wetting device 2126 along a central axis thereof. In general, the catheter tube 2110 will move through the housing opening 2142 to be wetted by the wetting applicator 2150 and through the distal end of the locator tip 2134 after the urethra is located by the locator tip 2134.

Figure 5:
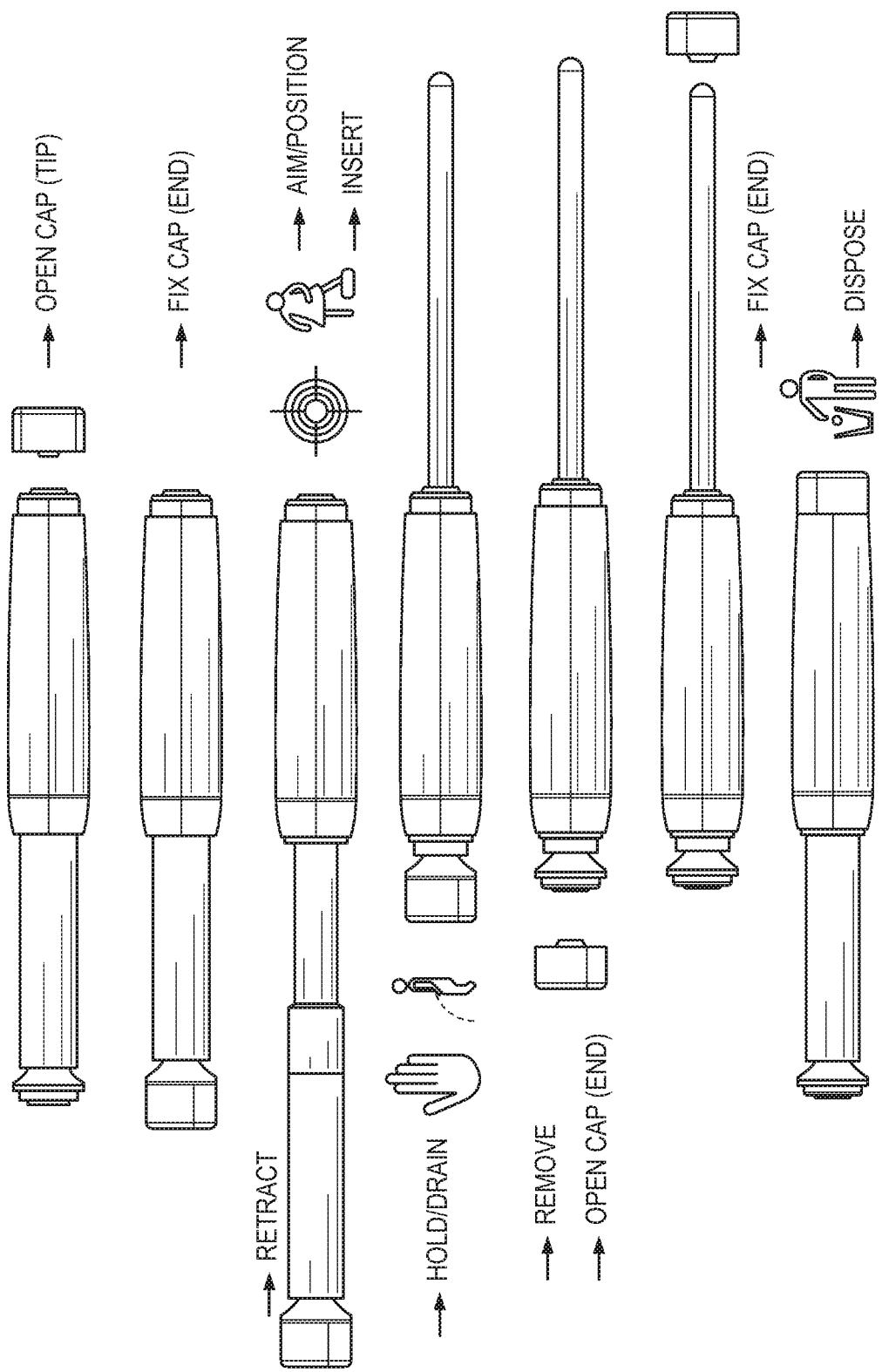
FIG. 5 illustrates an exemplary sequence of using a female catheter with a locator tip.

FIG. 5 depicts, from top to bottom, a sequence of events during use of a catheter assembly disclosed herein. First, a cap may be removed from the distal end of the device to reveal the locator tip. The cap may be pulled off or twisted off, as the case may be. Next, the cap may be fixed to the proximal end of the catheter assembly. An actuator is retracted and the locator tip is used to target the urethra. Once the urethra is found, the actuator is pushed through the catheter housing and through the locator tip. The user may then relieve himself/herself of urine. The cap may be removed before or after relieving, at least in some cases. Additionally, the cap may be used to push the catheter tube back into the housing before disposal.

Figure 6:
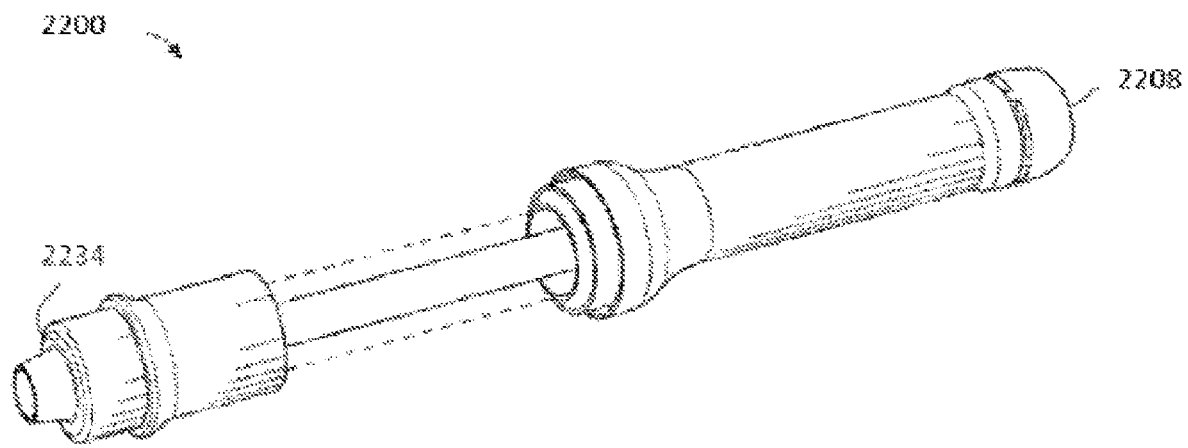
FIG. 6 illustrates a perspective view of an exemplary female catheter device with a locator tip in a position for targeting a urethra prior to insertion.

FIG. 6 depicts a female urethral catheter system 2200 prior to insertion of the urethral catheter tube (not shown) into the female subject. The female catheter system 2200 includes a proximal end 2208 and a locator tip 2234 disposed on a distal portion of the catheter system 2200. The catheter system 2200 shown in FIG. 6 may be used an alternative to the catheter systems shown in FIGS. 2-5, at least in some embodiments.

Figure 7:
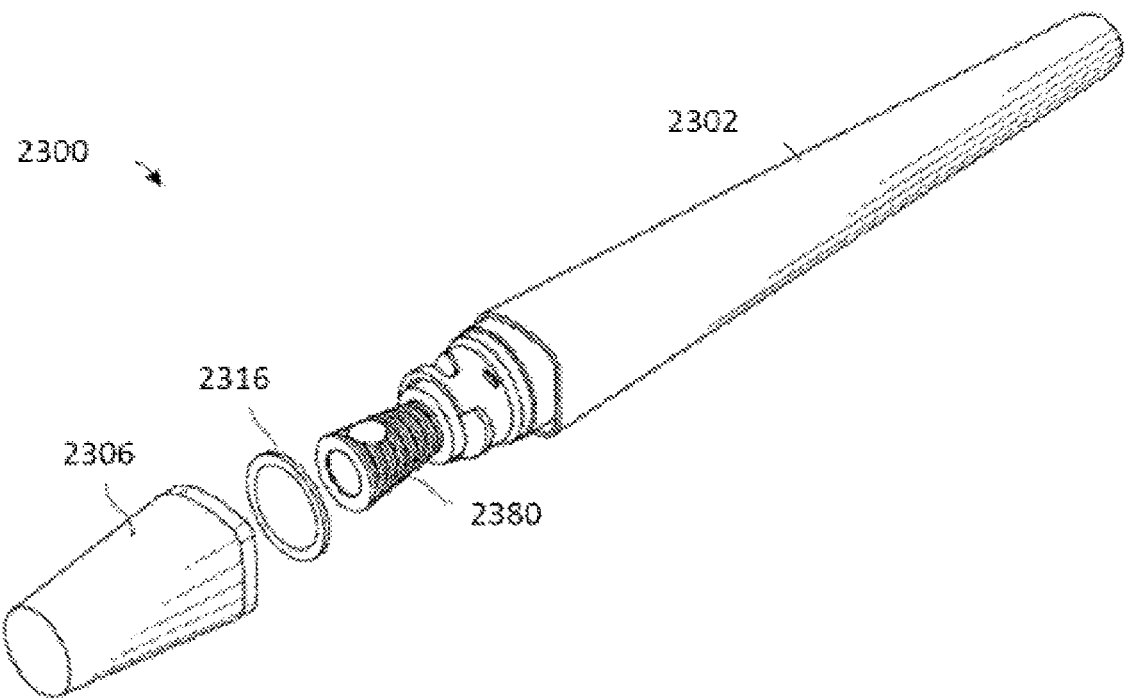
FIG. 7 illustrates an exploded view of a cap portion of an exemplary female urinary catheter.
Figure 8:
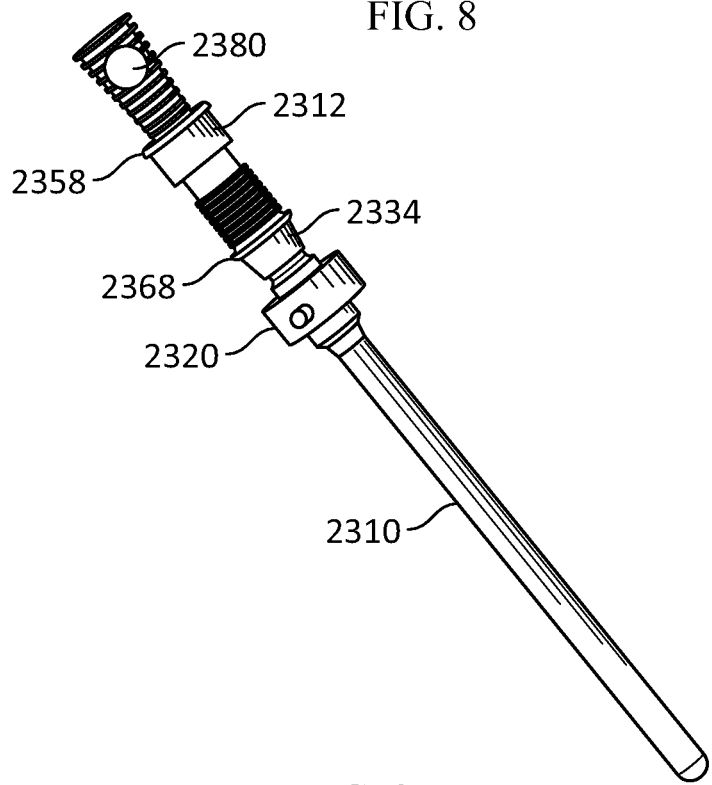
FIG. 8 illustrates an exemplary female urinary catheter including a wetting device and a locator tip with a case (not shown) removed.
Figure 9:
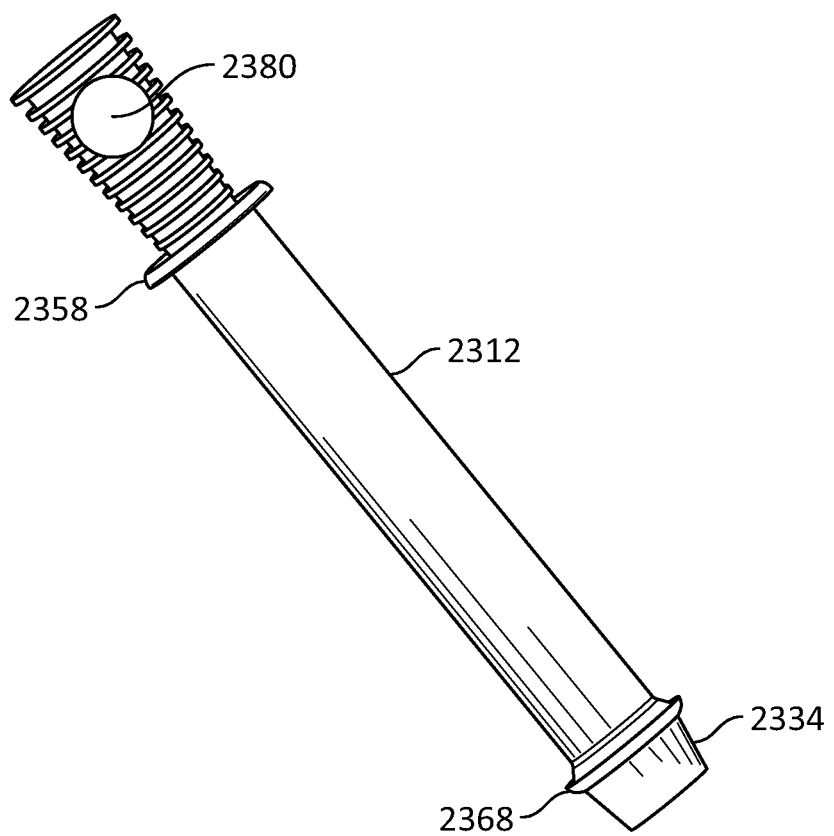
FIG. 9 illustrates an exemplary female urinary catheter having a locator tip in an extended state subsequent to extension of a sleeve and the locator tip over a tube of the catheter.

Referring now to FIGS. 7-9, in some embodiments, catheter assemblies may be packaged in a small and compact device that keeps the catheter tube sterile until use. FIG. 7 depicts an exploded view of a cap of a catheter assembly 2300 having a case containing a female urinary catheter with a locator tip. The case has a lid 2306, a seal 2316, and a catheter tube housing 2302. The seal 2316 may be embodied as, or otherwise include, an O-ring. When the lid 2306 is removed upon use, a funnel 2380 is exposed. The user may withdraw the catheter tube from the catheter tube housing 2302 such that the catheter tube may appear as depicted in FIG. 8 (e.g., see the catheter tube 2310). After use, the catheter tube may be reinserted into the catheter tube housing 2302 and the lid 2306 may be replaced. The seal 2316 is provided to prevent or resist any fluids from leaking until disposal of the assembly 2300.

FIG. 8 depicts a catheter tube assembly (e.g., the assembly 2300) prior to use where the catheter tube 2310 and the funnel 2380 are uncovered. A locator tip 2334 and concertina or accordion sleeve assembly 2312 may be located at the proximal portion of the catheter tube assembly. It should be appreciated that FIG. 8 may aid the viewer in understanding how the internal contents of the catheter assembly 2300 in FIG. 7 may appear. When removed from a case, the wetting device 2320 remains in the case such that the catheter tube 2310 may be drawn through the wetting device 2320 and wetted as the catheter tube assembly 2300 is withdrawn from the case. A gripper 2358 may be attached to the funnel 2380 to serve as a means to withdraw the catheter from its case, as well as a means to hold the catheter with locator tip base 2368 when the sleeve 2312 is extended over the catheter tube.

FIG. 9 depicts the catheter tube upon removal from the case in an extended state in which the sleeve 2312, together with the locator tip 2334, are drawn over the catheter tube 2310 to the distal end thereof. In some embodiments, the sleeve 2312 is connected to the locator tip 2334 directly or indirectly. Additionally, in some embodiments, the sleeve 2312 is connected to the locator tip 2334 via the locator tip base 2368.

Figure 10:
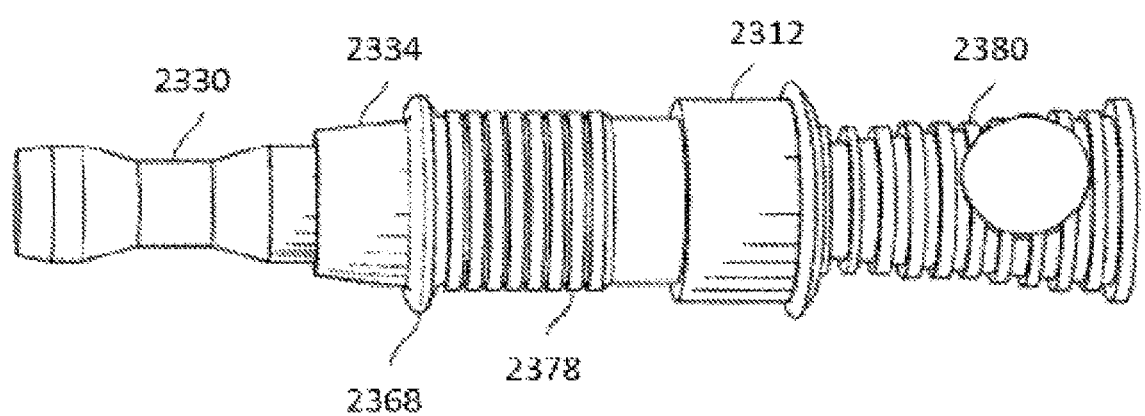
FIG. 10 illustrates an exemplary female urinary catheter having a locator tip in a retracted state.

FIG. 10 depicts a detailed view of the proximal end of a catheter assembly, such as the catheter assembly 2300 shown in FIG. 8, for example. It should be appreciated, however, that FIG. 8 does not show a wetting device enclosure. Instead, it shows a connector 2330 that is capable of moving through a wetting device and coupling to the catheter tube 2310 (not shown) and the funnel assembly 2380. The connector 2330 is typically connected to the catheter tube, at least in some embodiments. The connector 2330 may have a dumbbell appearance, and the wider ends of the connector 2330 may apply pressure to a wetting applicator of a wetting device to release a wetting agent onto a catheter tube as it follows the connector 2330 through the wetting device. Thus, according to FIG. 10, a user may grab the funnel 2380 and pull the catheter tube assembly, including the connector 2330 and the catheter tube 2310, out of the case. As the catheter tube assembly is removed from the case, the catheter tube 2310 is wetted with wetting agent and the sleeve 2312 is drawn over the connector 2330 and the catheter tube 2310 simultaneously or substantially simultaneously (e.g., see FIG. 9). After the catheter tube 2310 is removed from the case and the wetting device, the user may continue to hold the sleeve 2312, the locator tip base 2368, and a locator tip grip 2378 covered by the sleeve 2312. In some embodiments, with his/her other hand, the user may guide the locator tip to the urethra while keeping the catheter tube 2310 sterile. Once the urethra is located, the user may apply force to the funnel 2380 to move it towards the locator tip, thereby moving the catheter tube 2310 through the locator tip and into the urethra.

Catheter Wetting Devices

In some embodiments, an accessory includes a urinary catheter assembly having a wetting device. One such assembly is disclosed in International Application No. PCT/US18/67363.

In some embodiments, a urinary catheter assembly of the present disclosure includes (i) a urinary catheter having a distal end configured to be inserted into a urethra to evacuate a bladder, a proximal end, and a length therebetween, and (ii) a catheter case. In some embodiments, the catheter case includes a top and a bottom joined together to provide the catheter case with a length and a width, an opening through the top for removal and/or re-insertion of the urinary catheter from and into the catheter case, and a guiding element disposed in at least one of the top and the bottom that is configured to maintain at least a portion of the urinary catheter in a curved configuration until use. Additionally, in some embodiments, the guiding element is configured to control the path of the urinary catheter during removal and re-insertion of the urinary catheter from and into the catheter case.

In some embodiments, at least a portion of the curved configuration of the urinary catheter has an "S" shape. Additionally, in some embodiments, at least a portion of the curved configuration of the urinary catheter has an "8" shape. In some embodiments still, the curved configuration of the urinary catheter does not include more than two turns. In some embodiments yet still, a region of the urinary catheter most proximal to the distal end of the urinary catheter is straight. In some cases, the region is about 5 cm to about 15 cm in length. Furthermore, in some embodiments, the guiding element is a bearing in a configuration that is the same as at least a portion of the curved configuration of the urinary catheter.

In some embodiments, a urinary catheter assembly of the present disclosure includes a lid configured to close the opening to provide a fluid tight seal to the catheter case. Additionally, in some embodiments, the lid is connected to the top by a hinge. Furthermore, in some embodiments, the hinge is offset clockwise or counter-clockwise relative to a center line of the assembly. For example, the hinge may be offset relative to the center line by at least 15 degrees, by at least 30 degrees, by at least 45 degrees, by at least 60 degrees, by at least 75 degrees, or by at least 90 degrees. In some embodiments still, the urinary catheter assembly disclosed herein includes a hollow funnel connected to the proximal end thereof that is configured to be held while the distal end is inserted into the urethra. In some embodiments yet still, the hollow funnel has a substantially circular configuration at the proximal end thereof and tapers to a flattened, substantially oval configuration at an opposite end thereof that forms a spout. In such embodiments, the hollow funnel may have a substantially circular configuration at the proximal end and a substantially circular configuration at the opposite end that forms a spout. In some cases, the spout end of the hollow funnel may have semi-major and semi-minor axes that are substantially equal.

In some embodiments, the urinary catheter assembly of the present disclosure includes an expandable sleeve disposed around the catheter that has a first sleeve end connected to the funnel and a second sleeve end disposed away from the funnel. Additionally, in some embodiments, the expandable sleeve is compressed in an unexpanded state prior to use of the urinary catheter. In some embodiments still, the urinary catheter assembly includes a slidable gripper disposed around the catheter that has a first gripper end connected to the second sleeve end and a free second gripper end.

In some embodiments, the urinary catheter assembly of the present disclosure includes a wetting device having a front and a back that form a volume therebetween and that each has an opening disposed and configured to allow the catheter to pass therethrough. Additionally, in some embodiments, the urinary catheter assembly includes a wetting applicator having a liquid absorbed therein that is disposed in the volume. In such embodiments, the wetting applicator has an opening extending therethrough that is configured to supply the liquid to a surface of the urinary catheter as the urinary catheter passes through the openings in the front and the back of the wetting device. In some embodiments still, the wetting device is disposed adjacent the free gripper end to maintain compression of the expandable sleeve in an unexpanded state prior to use. In some embodiments yet still, the opening of the wetting applicator is smaller than the openings in the front and the back of the wetting device. Further still, in some embodiments, prior to use, the hollow funnel passes through the opening in the wetting applicator and through the openings in the front and the back of the wetting device to provide a fluid tight seal to the wetting device. In some cases, the urinary catheter assembly includes an O-ring located between the outer edges of the top and the bottom to provide a seal that maintains sterility of the catheter tube until use. In other cases, however, the urinary catheter assembly includes an O-ring located between the top and bottom inner edges of a handle in the catheter case.

In some embodiments, to maintain sterility of the catheter assemblies disclosed herein, the top and bottom outer edges of the assembly may be sealed using laser welding. Once welded, the resultant seal maintains sterility of the catheter tube until use, at least in some embodiments. Additionally, in some embodiments, once welded, the resultant seal maintains a sterile barrier after sterilization of the urinary catheter assembly. In such embodiments, the materials used in conjunction with laser welding are selcted to allow a laser to pass through the assembly region in the vicinity of where the laser weld(s) are required.

In some embodiments, laser welding may be performed with a diode laser at a wavelength of from 850 to 1100 nm, from 900 to 1050 nm, from 960 to 1010 nm wavelength, or a 980 nm wavelength. In one example, if the catheter assembly is sealed using laser welding, the top of the catheter case may be laser absorbing, and the bottom of the case may be laser translucent. However, in another example, the bottom of the catheter case may be laser absorbing and the top of the case may be laser translucent if laser welding is performed.

As contemplated by the present disclosure, materials that are capable of allowing a laser to pass therethrough to produce a laser weld to facilitate sterilization include, but are not limited to, laser transparent or laser translucent plastic or resin, such as a polypropylene (PP) containing an organic pigment, a polyphenylene ether (PPE) containing an organic pigment, a polycarbonate (PC) containing an organic pigment, or an acrylonitrile butadiene styrene (ABS) containing an organic pigment, for example. In some embodiments, the laser passes through a laser translucent plastic. Additionally, in some embodiments, the material that allows a laser to pass through may also include reduced amounts of (or zero) black or laser absorbing pigment (e.g., iron oxide or carbon black). The removal of black or laser absorbing pigment reduces the amount of laser energy absorbed by the material, thereby allowing increased energy to pass through the assembly region being laser welded. In some embodiments, the top and/or bottom of a laser absorbing catheter case may include plastic or resin, which may be, for example, a polypropylene (PP) containing an inorganic pigment (e.g., iron oxide) or carbon black, a polyphenylene ether (PPE) containing an inorganic pigment or carbon black, a polycarbonate (PC) containing an organic pigment or carbon black, or an acrylonitrile butadiene styrene (ABS) containing the organic pigment or carbon black.

In some embodiments, the urinary catheter assemblies of the present disclosure may be sterilized after manufacture by exposure to e-beam or gamma radiation. Sterilization may occur when the urinary catheter assembly is packaged and/or ready for shipment, at least in some embodiments.

In some embodiments, any urinary catheter disclosed herein includes, or is integrated with, a polymer, such as a hydrophilic polymer, for example. Additionally, in some embodiments, the urinary catheter is coated with a polymer, such as a hydrophilic polymer, in one example. In some embodiments still, the urinary catheter includes, or is integrated with, a polymer mixture of a thermoplastic or thermo-curing polymer base material and an amphiphilic block copolymer, such as the mixture disclosed in WIPO Publication No. 2011/051439. Further still, in some embodiments, the urinary catheter is coated with the polymer mixture of a thermoplastic or thermo-curing polymer base material and amphiphilic block copolymer (e.g., as disclosed in WIPO Publication No. 2011/051439).

In some embodiments, an accessory of the present disclosure includes a catheter case for storing and dispensing a urinary catheter and a wetting device. In some embodiments, the catheter case includes a top and a bottom joined together to provide the catheter case with a length and a width, an opening through the top for removal and/or re-insertion of the urinary catheter from and into the catheter case, and a guiding element disposed in at least one of the top and the bottom. In some embodiments, the guiding element is configured to maintain at least a portion of the urinary catheter in a curved configuration until use. Additionally, in some embodiments, the guiding element is configured to control the path of the urinary catheter during removal and re-insertion of the urinary catheter from and into the catheter case.

In some embodiments, catheter cases disclosed herein include a lid configured to selectively provide access to an opening for removal and/or reinsertion of the urinary catheter from and into the catheter case. Additionally, in some embodiments, the lid is connected to the top by a hinge. Further, in some embodiments, the hinge is offset clockwise or counterclockwise relative to a center line of the catheter case (e.g., by at least 15 degrees, by at least 30 degrees, by at least 45 degrees, by at least 60 degrees, by at least 75 degrees, or by at least 90 degrees). Further still, in some embodiments, the lid is configured to close the opening to provide a fluid tight seal to the catheter case. In some cases, the lid includes a tab connected to the lid by a joint. Additionally, in some cases, the tab is configured to be bent away from the catheter case and to create a grip to open the lid. In some cases still, bending of the tab creates a fatigue mark in the joint that provides a visible tamper-evident indication.

In some embodiments, the lid includes a first engaging member that interacts with a second engaging member situated at, or otherwise provided at, the top of the catheter case. The first and/or second engaging members may each be embodied as, or otherwise include, a bump, clip, notch, or any protrusion or depression configured to interact with the other engaging member to close the catheter lid. In an exemplary embodiment, after re-insertion of the urinary catheter into the catheter case, the lid is closed by pressing the first engaging member of the lid against the top of the catheter case to enclose the urinary catheter within the catheter case. In some cases, minimal or no liquid from the catheter is released from the catheter case when the lid is closed.

In some embodiments, the tab is connected to the catheter case using an ultrasonic weld, and moving the tab away from the catheter case irreversibly and noticeably damages the ultrasonic weld to provide a visible tamper-evident indication. In some instances, catheter cases disclosed herein include a seal that covers the opening and a connecting tab disposed on an upper surface of the seal that is adhered to an underside of lid so that the seal is peeled open as the lid is opened to provide a visible tamper-evident indication. In other instances, catheter cases disclosed herein include a seal that covers the opening without a connecting tab being present, and a user manually has to open the seal separately from the lid. The seal continues to provide a visible tamper-evident indication.

In some embodiments, the lid and the top of the catheter case include mating elements in the forms of a clip feature on the lid and a notch feature on the top to provide a labyrinthine pathway to prevent egress of liquid droplets from a closed or re-closed catheter case. Additionally, in some embodiments, the lid is sealed using an exterior paper-type seal that is placed on either the exterior top or bottom face of the assembly. In some embodiments still, the lid is sealed using an overlapping top and bottom face of the assembly, which clicks into place to lock the top and bottom faces of the assembly together. Furthermore, in some embodiments, the labyrinthine pathway prevents or resists egress of liquid droplets from the closed catheter case. In some instances, catheter cases disclosed herein comprise a labyrinthine pathway to prevent egress of liquid droplets that is formed by a plurality of protrusions projecting from the lid toward the opening. In some instances, one of the plurality of protrusions contacts the seal and another of the plurality of protrusions projects into a channel adjacent the opening.

In some embodiments, at least a portion of the guiding element forms a generally "S"-shaped curved configuration. Additionally, in some embodiments, the guiding element crosses itself not more than once and reverses direction not more than twice. In some embodiments still, the top and the bottom of the catheter assembly each have a generally oval shape, and the opening has a generally circular shape. In some embodiments yet still, the guiding element includes a first plurality of ribs disposed on each of the top and the bottom of the catheter assembly. Further, in some embodiments, the first plurality of ribs on each of the top and the bottom match each other.

In some instances, catheter cases of the present disclosure include a wetting device having a front and a back that form a volume therebetween. Each of the front and the back has an opening disposed and configured to allow the catheter to pass therethrough, at least in some embodiments. Additionally, in some embodiments, catheter cases of the present disclosure include a retaining element disposed in at least one of the top and the bottom that is configured to retain the wetting device. In some embodiments still, the retaining element includes a second plurality of ribs disposed on each of the top and the bottom. Further, in some embodiments, the second plurality of ribs in each of the top and the bottom match each other.

Methods

In yet another aspect, methods for collecting fluid using any urine collection bag described herein are provided by the present disclosure. The methods may include providing a catheter connected to a urine collection bag, inserting the catheter into the urethra, and collecting urine in the urine collection bag. Additionally, among things, the method may include providing a catheter and a urine collection bag, inserting the catheter into the urethra, connecting the catheter to the urine collection bag, and collecting urine in the urine collection bag. In some cases, as the urine is drawn into the bag, the bag is positioned on a horizontal surface. In some cases still, as the urine is drawn into the bag, the bag is positioned vertically. After the urine is collected, the catheter is removed from the urethra and removed from the urine collection bag, at least in some embodiments. Further, in some embodiments, the neck of the urine collection bag is threaded through an aperture of the bag. The bag may be disposed of with the collected urine, or the bag may be torn open along a perforation line and the urine dispensed with in an appropriate receptacle.

In yet another aspect still, a method of manufacturing any urine collection bag described herein is contemplated by the present disclosure. In some embodiments, the method includes welding a first external layer to a first internal layer to generate a first assembly, welding a second external layer to a second internal layer to generate a second assembly, welding the first assembly to the second assembly to generate a combined assembly, and cutting the combined assembly to generate the collection bag. Additionally, in some embodiments, the first assembly and the second assembly are prepared concurrently. In some embodiments still, the first assembly and the second assembly are prepared sequentially. The welding steps may include the use of heat and pressure to combine the layers. In one example, the method of manufacture utilizes an apparatus comprising a welding tool and a cutting tool.

EXAMPLES

The examples and embodiments described herein are for illustrative purposes only and are not intended to limit the scope of the claims. It should be appreciated that various modifications or changes apparent to persons skilled in the art are within the spirit and purview of this application and scope of the appended claims.

Example 1

Method of Manufacturing

A fluid collection apparatus as generally depicted in FIG. 1 was manufactured. A first external layer of phthalate-free, transparent, PVC material having a thickness of 100 microns was printed with graphic elements. The first external layer was welded to a first internal layer of 100 microns thick PVC to create a first assembly. In parallel, a second external later of phthalate-free, transparent, PVC material having a thickness of 100 microns was welded to a second internal layer to create a second assembly. Welding was performed using an apparatus including a welding and a cutting tool in a single unit to ensure aligned weld and cut lines. While the assemblies were still in place within the apparatus, immediately following the welding, an outline of the urine collection bag was cut. Unused sections of the materials were removed, and the urine collection bag was removed from the apparatus.

Example 2

Collection of Urine using a Urinary Catheter System

The fluid collection apparatus of Example 1 was used to collect urine from patients. Patients noted the material of the bag was robust and tough, while feeling relatively soft to the touch.

While the disclosure has been illustrated and described in detail in the foregoing drawings and description, the same is to be considered as exemplary and not restrictive in character, it being understood that only illustrative embodiments thereof have been shown and described and that all changes and modifications that come within the spirit of the disclosure are desired to be protected.

The invention claimed is:

1. A urine collection bag comprising:
   an outer profile;
   an inner profile;
   first and second external layers sealed around a first periphery to define the inner profile, wherein the inner profile includes a container portion to hold urine and an elongated portion to receive a catheter through an opening thereof;
   a notch disposed at the opening to facilitate insertion of the catheter into the elongated portion;
   at least one webbing section positioned between the inner profile and the outer profile such that the at least one webbing section at least partially defines the notch; and
   a one-way valve,
   wherein:
   the first external layer is shorter than the second external layer in a location of the at least one webbing section to create the notch,
   the at least one webbing section includes a first region of the first external layer and the second external layer welded together in the elongated portion,
   the first region of the at least one webbing section extends inwardly into the elongated portion to define a neck of the elongated portion, the neck has a width that is less than a width of the opening, the first region of the at least one webbing section is devoid of any tear lines adjacent the neck, each of the neck and the one-way valve is spaced from the notch along a length of the elongated portion, and the neck is arranged between the notch and the one-way valve along the length of the elongated portion.

2. The urine collection bag of claim 1, wherein the first external layer and the second external layer are welded at the first periphery to define the inner profile.

3. The urine collection bag of claim 1, wherein the first external layer and the second external layer are sealed around a second periphery to define the outer profile, and wherein the first external layer and the second external layer are welded at the second periphery to define the outer profile.

4. The urine collection bag of claim 1, wherein the at least one webbing section includes a second region of the first external layer and the second external layer welded together in the container portion.

5. The urine collection bag of claim 4, wherein the second region of the at least one webbing section includes a first aperture.

6. The urine collection bag of claim 1, further comprising a first aperture, wherein the first aperture is positioned between the inner profile and the outer profile.

7. The urine collection bag of claim 6, wherein the elongated portion and the first aperture are arranged such that at least a portion of the elongated portion is threadable through the first aperture.

8. The urine collection bag of claim 5, wherein the at least one webbing section includes a third region of the first external layer and the second external layer welded together in the container portion.

9. The urine collection bag of claim 8, wherein the third region of the at least one webbing section includes a second aperture.

10. The urine collection bag of claim 1, further comprising a second aperture, wherein the second aperture is positioned between the inner profile and the outer profile.

11. The urine collection bag of claim 8, wherein the at least one webbing section includes a fourth region of the first external layer and the second external layer welded together in the container portion.

12. The urine collection bag of claim 11, wherein the fourth region of the at least one webbing section includes a perforated tear line.

13. The urine collection bag of claim 1, further comprising a perforated tear line, wherein the perforated tear line is positioned between the inner profile and the outer profile.

14. The urine collection bag of claim 1, wherein the one-way valve includes a first internal layer and a second internal layer positioned within the elongated portion.

15. The urine collection bag of claim 14, wherein the first internal layer and the second internal layer are welded between the first external layer and the second external layer.

16. The urine collection bag of claim 15, wherein in use, the catheter is positioned between the first internal layer and the second internal layer.

17. The urine collection bag of claim 16, wherein the first internal layer includes one or more welds.

18. The urine collection bag of claim 17, wherein the first internal layer, the second internal layer, the first external layer, and the second external layer are sealed together on two or more sides of each layer, and wherein the seal includes a weld.

19. The urine collection bag of claim 1, wherein the elongated portion includes a tapered profile, and wherein the tapered profile is formed by welding the first external layer with the second external layer.

20. The urine collection bag of claim 1, wherein a bottom of the container portion is folded.

21. The urine collection bag of claim 1, wherein the urine collection bag is capable of standing upright when filled with at least 20% fill capacity.

22. The urine collection bag of claim 1, wherein the container portion includes at least four sides, wherein not one of the at least four sides is parallel to another one of the at least four sides, and wherein at least two of the at least four sides are at least substantially straight.

23. The urine collection bag of claim 1, wherein the first region of the at least one webbing section is devoid of apertures.

24. The urine collection bag of claim 1, wherein:

the first region of the at least one webbing section includes one sub-region and another sub-region spaced from the one sub-region across the width of the neck, and each of the one sub-region and the another sub-region extends free of any tear lines along a length of the elongated portion from the notch to the neck.

25. The urine collection bag of claim 24, wherein the one sub-region and the another sub-region cooperatively define the neck such that the neck is free of any tear lines.

* * * * *